United States Patent
Marshall

(10) Patent No.: US 10,155,023 B2
(45) Date of Patent: Dec. 18, 2018

(54) CONFORMATIONALLY SPECIFIC VIRAL IMMUNOGENS

(71) Applicant: CALDER BIOSCIENCES INC., New York, NY (US)

(72) Inventor: Christopher Patrick Marshall, New York, NY (US)

(73) Assignee: CALDER BIOSCIENCES INC., New York, NY (US)

(*) Notice: Subject to any disclaimer, the term of this patent is extended or adjusted under 35 U.S.C. 154(b) by 0 days.

(21) Appl. No.: 15/424,107

(22) Filed: Feb. 3, 2017

(65) Prior Publication Data

US 2018/0117116 A1    May 3, 2018

Related U.S. Application Data

(63) Continuation of application No. 13/890,465, filed on May 9, 2013.

(60) Provisional application No. 61/644,830, filed on May 9, 2012.

(51) Int. Cl.
| | |
|---|---|
| *C12N 7/00* | (2006.01) |
| *A61K 39/12* | (2006.01) |
| *A61K 38/16* | (2006.01) |
| *C07K 14/005* | (2006.01) |

(Continued)

(52) U.S. Cl.
CPC .......... *A61K 38/162* (2013.01); *C07K 14/005* (2013.01); *C12N 7/00* (2013.01); *C12P 21/00* (2013.01); *G01N 33/56988* (2013.01); *C12N 2740/16051* (2013.01); *C12N 2740/16122* (2013.01); *C12N 2740/16134* (2013.01)

(58) Field of Classification Search
None
See application file for complete search history.

(56) References Cited

U.S. PATENT DOCUMENTS

| | | |
|---|---|---|
| 6,534,064 B1 | 3/2003 | O'Hagan |
| 7,037,894 B2 | 5/2006 | Marshall |
| 7,179,468 B1 | 2/2007 | Lu |

(Continued)

FOREIGN PATENT DOCUMENTS

| | | |
|---|---|---|
| WO | 2001029247 A1 | 4/2001 |
| WO | 2007149491 A1 | 12/2007 |

OTHER PUBLICATIONS

Beddows et al.; Construction and Characterization of Soluble, Cleaved, and Stabilized Trimeric Env Proteins Based on HIV Type I Env Subtype A; AIDS Res. Hum. Retroviruses; 2006; 22(6); 569-579.

(Continued)

*Primary Examiner* — Janet L Andres
*Assistant Examiner* — M Franco G Salvoza
(74) *Attorney, Agent, or Firm* — Grimes & Yvon LLP

(57) ABSTRACT

The present invention provides methods of making engineered viral proteins and protein complexes that are useful as vaccine immunogens, engineered viral proteins and protein complexes made using such methods, and pharmaceutical compositions comprising such engineered viral proteins and protein complexes. Such engineered viral proteins and protein complexes may comprise one or more cross-links that stabilize the conformation of an antibody epitope, such as a quaternary neutralizing antibody, and may exhibit an enhanced ability to elicit a protective immune response when administered to a subject as a component of a vaccine.

8 Claims, 2 Drawing Sheets

(51) Int. Cl.
 *C12P 21/00* (2006.01)
 *G01N 33/569* (2006.01)

(56) References Cited

U.S. PATENT DOCUMENTS

| | | |
|---|---|---|
| 7,311,920 B1 | 12/2007 | Devico |
| 2005/0054572 A1 | 3/2005 | Marshall |
| 2006/0165715 A1 | 7/2006 | Clore |
| 2008/0206264 A1 | 8/2008 | Anglister |
| 2009/0092582 A1 | 4/2009 | Bogin |
| 2011/0076298 A1 | 3/2011 | Olson |
| 2011/0123556 A1 | 5/2011 | Phogat |
| 2013/0149336 A1 | 6/2013 | Hjelle |
| 2013/0236905 A1 | 9/2013 | Marshall |

OTHER PUBLICATIONS

Beddows et al.; A comparative immunogenicity study in rabbits of disulfide-stabilized proteolytically cleaved, soluble trimeric human immunodeficiency virus type 1 gp140, trimeric cleavage-defective gp140 and momomeric gp120; Virol.; Apr. 10, 2007; 360; 329-340.
Dey et al.; Characterization of Human Immunodeficiency Virus Type 1 Monomeric and Trimeric gp120 Glycoproteins Stabilized in the CD4-Bound State: Antigenicity, Biophysics, and Immunogenicity; J. Virol.; Mar. 14, 2007; 81(11); p. 5579-5593.
Endrizzi et al; Specific Covalent Immobilization of Proteins through Dityrosine Cross-Links; Langmuir; 2006; 22; 11305-11310.
Farzan et al.; Stabilization of Human Immunodeficiency Virus Type 1 Envelope Glycoprotein Trimers by Disulfide Bonds Introduced into the gp41 Glycoprotein Ectodomain; J. Virol.; 1998; 72(9); 7620-25.
Fouts et al.; Crosslinked HIV-1 envelope—CD4 receptor complexes elicit broadly cross-reactive neutralizing antibodies in rhesus macaques; PNAS; Sep. 3, 2002; 99 (18) p. 11842-11847.
Haim et al.; Proteolytic Processing of the Human Immunodeficiency Virus Envelope Glycoprotein Precursor Decreases Conformational Flexibility; J. Virol.; Feb. 2013; vol. 87 No. 3; 1884-1889.
Hinton et al.; Pattern recognition by B cells: the role of antigen repetitiveness versus Toll-like receptors; Curr. Top. Microbiol. Immunol.; 2008; 319; pp. 1-15.
Horowitz et al.; Tyrosine Cross-Linking Reveals Interfacial Dynamics in AdenoAssociated Viral Capsids during Infection; ACS Chem. Biol.; 2012; 7; 1059-1066.
Jeffs et al.; Expression and characterisation of recombinant oligomeric envelope glycoproteins derived from primary isolates of HIV-1;Vaccine; 2002; 22:1032-1046.
Kwong et al.; HIV-1 evades antibody-mediated neutralization through conformational masking of receptor-binding sites; Nature; 2002; 420; 678-82.
Kwong et al.; Rational Design of Vaccines to Elicit Broadly Neutralizing Antibodies to HIV-1; Cold Spring Harb. Perspect. Med.; 2011; 1:a007278.
Liu et al.; Molecular architecture of native HIV-1 gp 120 trimers; Nature; 2008; 455(7209); 109-113.
Meunier et al.; Crosslinking of and coupling to viral capsid proteins by tyrosine oxidation; Chem. Biol.; 2004; 11(3); 319-26.
Phogat et al.; Rational modifications of HIV-1 envelope glycoproteins for immunogen design; Curr. Pharm. Design; 2007;13; 213-227.
Sanders et al.; Stabilization of the Soluble, Cleaved, Trimeric Form of the Envelope Glycoprotein Complex of Human Immunodeficiency Virus Type 1; Journal of Virology, Sep. 2002; p. 8875-8889.
Schulke et al.; Oligomeric and conformational properties of a proteolytically mature, disulfide-stabilized human immunodeficiency virus type 1 gp140 envelope glycoprotein; 2002.; J. Virol.; 76; 7760-7776.
Spohn et al.; A VLP-based vaccine targeting domain III of the West Nile virus E protein protects from lethal infection in mice; Virology Journal; 2010; 7: p. 1.
Extended European Search Report for European Patent Application No. 13787969.8; dated Jun. 3, 2015.
International Search Report for International Patent Application No. PCT/US2013/040228; dated Sep. 30, 2013.
OEE Work Product for Consideration with Patent Prosecution Highway Request; Office Action from European Patent Application No. 13787969.8.

CONFORMATIONALLY SPECIFIC VIRAL IMMUNOGENS

This application is a continuation of U.S. application Ser. No. 13/890,465, filed on May 9, 2013, which claims the benefit of U.S. Provisional Patent Application No. 61/644,830, filed May 9, 2012, the contents of each of which are hereby incorporated by reference.

STATEMENT REGARDING FEDERALLY SPONSORED RESEARCH

This invention was made with government support under NIH grant number AI091507 awarded by the National Institutes of Health. The government has certain rights to the invention.

A portion of the disclosure of this patent document contains material which is subject to copyright protection. The copyright owner has no objection to the facsimile reproduction by anyone of the patent document or the patent disclosure as it appears in the Patent and Trademark Office patent file or records, but otherwise reserves all copyright rights whatsoever.

FIELD OF THE INVENTION

The present invention relates, in part, to methods of producing conformationally-specific immunogens, and methods of producing engineered viral proteins and protein complexes useful as conformationally-specific immunogens, and to conformationally-specific immunogens and engineered viral proteins and protein complexes produced using such methods.

BACKGROUND OF THE INVENTION

Many pathogenic viruses have developed strategies to evade recognition and elimination by host immune systems. Such strategies include high mutation rates of envelope glycoproteins, glycosylation of envelope proteins, and conformational masking—whereby conserved portions of viral proteins, such as those involved in key functions such as receptor binding, are "masked" such that they are poorly recognized by, or evade recognition by, antibodies. Such conformational masking poses a major problem in the development of vaccines based on viral proteins. Hence there is a need in the art for methods of producing engineered viral proteins, and complexes of viral proteins, that have enhanced immunogenicity and enhanced effectiveness as vaccines.

SUMMARY OF THE INVENTION

The present invention provides, in part, methods for producing conformationally-specific vaccine immunogens, methods of engineering viral proteins and protein complexes, viral proteins and protein complexes so engineered, and pharmaceutical compositions comprising such engineered viral proteins and protein complexes. Such engineered proteins may be useful as conformationally-specific vaccine immunogens.

In one embodiment the present invention provides a method for producing a conformationally-specific immunogen, the method comprising: (a) obtaining a viral protein or protein complex in one or more conformations that favor the elicitation of protective immune responses, (b) identifying one or more regions in the tertiary and/or quaternary structure of the viral protein or protein complex in which the introduction of one or more cross-links could stabilize the conformation of an antibody epitope (and/or could stabilize a conformation that favors the elicitation of a protective immune response), and (c) introducing into the viral protein or protein complex one or more targeted cross-links at one or more of the regions identified in step (b) to form an engineered viral protein or protein complex, wherein the engineered viral protein or protein complex has one or more of the following properties: (i) enhanced ability bind to a neutralizing antibody as compared to the viral protein or protein complex (i.e. as compared to the viral protein or protein complex without or before introduction of the cross-links), (ii) enhanced ability bind to a broadly neutralizing antibody as compared to the viral protein or protein complex, (iii) enhanced ability bind to and activate B cell receptors as compared to the viral protein or protein complex, (iv) enhanced ability to elicit an antibody response in an animal as compared to the viral protein or protein complex, (v) enhanced ability to elicit a protective antibody response in an animal as compared to the viral protein or protein complex, (vi) enhanced ability to elicit production of neutralizing antibodies in an animal as compared to the viral protein or protein complex, (vii) enhanced ability to elicit production of broadly neutralizing antibodies in an animal as compared to the viral protein or protein complex, (viii) enhanced ability to elicit a protective immune response in an animal as compared to the viral protein or protein complex, and (ix) enhanced ability to bind to and elicit production of antibodies that recognize quaternary neutralizing epitopes in an animal as compared to the viral protein or protein complex. In some such embodiments the targeted cross-links are dityrosine (DT) cross-links.

In another embodiment the present invention provides a method for producing a conformationally-specific immunogen, the method comprising: (a) obtaining a viral protein or protein complex in one or more conformations that favor the elicitation of protective immune responses, and (b) introducing into the viral protein or protein complex one or more cross-links that are stable under physiological conditions, wherein the engineered viral protein or protein complex has one or more of the following properties: (i) enhanced ability bind to a neutralizing antibody as compared to the viral protein or protein complex (i.e. as compared to the viral protein or protein complex without or before introduction of the cross-links), (ii) enhanced ability bind to a broadly neutralizing antibody as compared to the viral protein or protein complex, (iii) enhanced ability bind to and activate B cell receptors as compared to the viral protein or protein complex, (iv) enhanced ability to elicit an antibody response in an animal as compared to the viral protein or protein complex, (v) enhanced ability to elicit a protective antibody response in an animal as compared to the viral protein or protein complex, (vi) enhanced ability to elicit production of neutralizing antibodies in an animal as compared to the viral protein or protein complex, (vii) enhanced ability to elicit production of broadly neutralizing antibodies in an animal as compared to the viral protein or protein complex, (viii) enhanced ability to elicit a protective immune response in an animal as compared to the viral protein or protein complex, and (ix) enhanced ability to bind to and elicit production of antibodies that recognize quaternary neutralizing epitopes in an animal as compared to the viral protein or protein complex. In some such embodiments the cross-links are targeted to identified and/or selected positions within the protein or protein complex's tertiary or quaternary structure. In some such embodiments the targeted cross-links comprise dityrosine (DT) cross links.

In some embodiments where DT cross-links are used, at least one of the dityrosine cross-links originates from a point mutation of an amino acid residue to tyrosine. Furthermore, in some embodiments where DT cross-links are used, the methods described above further comprise introducing one or more point mutations to tyrosine into the viral protein or protein complex at one or more specific and/or identified regions before introducing dityrosine cross-links.

In some embodiments the methods of the invention further comprise performing an assay to assess the ability of the engineered viral protein or protein complex to bind to a neutralizing antibody, bind to a broadly neutralizing antibody, bind to and activate B cell receptors, elicit an antibody response in an animal, elicit a protective antibody response in an animal, elicit production of neutralizing antibodies in an animal, elicit production of broadly neutralizing antibodies in an animal, elicit a protective immune response in an animal, and/or elicit production of antibodies that recognize quaternary neutralizing epitopes in an animal.

In some embodiments the engineered viral proteins or protein complexes made using the methods of the invention are useful as a vaccine immunogens in animal subjects. In some embodiments the engineered viral proteins or protein complexes made using the methods of the invention are useful as a vaccine immunogens in mammalian subjects. In some embodiments the engineered viral proteins or protein complexes are useful as a vaccine immunogens in human subjects.

The methods of the present invention can be used to engineer proteins from numerous different viruses. In some embodiments the viral proteins or protein complexes are derived from a virus from the group consisting of Herpesvirales, Ligamenvirales, Mononegavirales, Nidovirales, Picornavirales, Lentiviruses, Human Immunodeficiency Viruses, Retroviruses, Orthomyxoviruses, Paramyxovirus, Influenza viruses, Poxviruses, Flaviviruses, Togaviruses, Coronaviruses, Rhabdoviruses, Bunyaviruses, Filoviruses, Reoviruses, Mononegavirales, Hepadnaviruses, and Hepatitis viruses. In some embodiments any viral protein may be engineered using the methods of the invention. In some embodiments the viral protein or protein complex to be engineered is a viral envelope protein or protein complex.

In some embodiments the engineered viral proteins or protein complexes of the invention are soluble. In some embodiments the engineered viral proteins or protein complexes of the invention form aggregates to a lesser degree or not at all, for example during the production process or when stored at a high concentration, by comparison to a protein or protein complex not so engineered.

In some embodiments the present invention provides pharmaceutical compositions comprising the engineered viral proteins or protein complexes of the invention. In some embodiments such compositions comprise a pharmaceutically effective amount of the engineered viral proteins or protein complexes. In some embodiments such compositions also comprise a pharmaceutically acceptable carrier. In some embodiments such compositions also comprise an adjuvant.

In some embodiments, the present invention provides methods for stabilizing envelope proteins and protein complexes of pathogenic viruses to enhance their effectiveness as vaccine immunogens. In one embodiment, the present invention provides methods by which tertiary structures of proteins and/or quaternary structures of protein complexes (i.e. protein-protein interactions in a complex of two or more proteins) can be stabilized by crosslinking, whereby the crosslinks are stable under physiologically relevant conditions, do not lead to aggregate formation of the proteins or protein complexes during expression or when they are stored in high concentrations, and stabilizes the folds of the proteins or protein complexes in particular conformations that can increase the effectiveness of the proteins or protein complexes as vaccine immunogens—for example by stabilizing epitopes in such conformations that can be recognized by antibodies and/or activate B cell receptors upon binding. In some such embodiments the crosslinks can be specifically directed to particular residues within the proteins or protein complexes, such as, for example, by dityrosine bonds, or the crosslinks can be directed to amino and sulfhydryl containing amino acid side chains. In some such embodiments the crosslinks can be zero-length, or may insert additional atoms and elements into the structure of the protein. In some embodiments, the present invention provides methods by which proteins or protein complexes can be oligomerized by oligomerization motifs that can stabilize protein complexes, and also stabilize the folds of the proteins in such protein complexes in particular conformations, such as those that increase the effectiveness of the proteins or protein complexes as vaccine immunogens, for example by stabilizing epitopes in conformations that can be recognized by antibodies and activate B cell receptors upon binding.

These and other embodiments of the invention are described throughout the present application, including in the Summary of Invention, Detailed Description, Examples, and Claims sections of the application. Furthermore, the various embodiments described herein can be combined and modified in various ways, as will be apparent to those of ordinary skill in the art, and such combinations and modifications are within the scope of the invention.

BRIEF DESCRIPTION OF THE DRAWINGS

FIG. 1A—Bar graph showing the results of a dityrosine (DT) specific spectrofluorometry experiment which was used to identify and quantify DT crosslinks in wild type control ("WT control") HIV Env gp140 protein and an engineered HIV Env gp140 protein having tyrosine substitution(s) in the V1/V2 region ("mutant"), both before and after (+DT) dityrosine crosslinking. FIG. 1B—Left panel—Coomassie staining of the mutant HIV Env gp140 protein without ("−") or with ("+") DT cross-linking. FIG. 1A-B—Right panel—Western blot of purified HIV Env gp140 without ("−") or with ("+") DT cross-linking. Arrows indicate the locations of the monomeric and trimeric forms.

DETAILED DESCRIPTION OF THE INVENTION

Figure 1A:
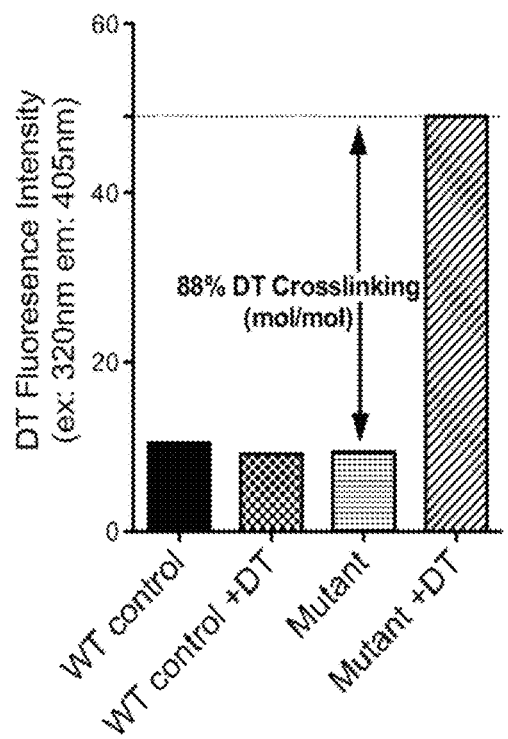
FIG. 1A-B. Analysis of dityrosine cross-linked HIV Env gp140 trimers.

The present invention provides, in part, methods of engineering viral proteins and protein complexes, viral proteins and protein complexes so engineered, and pharmaceutical compositions comprising such engineered viral proteins and protein complexes. Such engineered proteins may be useful as conformationally-specific immunogens.

In one embodiment the present invention provides a method for producing a conformationally-specific vaccine immunogen, the method comprising: (a) obtaining a viral protein or protein complex in one or more conformations that favor the elicitation of protective immune responses, (b) identifying one or more regions in the tertiary and/or quaternary structure of the viral protein or protein complex in which the introduction of one or more cross-links could stabilize the conformation of an antibody epitope (and/or could stabilize a conformation that favors the elicitation of a protective immune response), and (c) introducing into the viral protein or protein complex one or more targeted cross-links at one or more of the regions identified in step (b) to form an engineered viral protein or protein complex, wherein the engineered viral protein or protein complex has one or more of the following properties: (i) enhanced ability bind to a neutralizing antibody as compared to the viral protein or protein complex (i.e. as compared to the viral protein or protein complex without or before introduction of the cross-links), (ii) enhanced ability bind to a broadly neutralizing antibody as compared to the viral protein or protein complex, (iii) enhanced ability bind to and activate B cell receptors as compared to the viral protein or protein complex, (iv) enhanced ability to elicit an antibody response in an animal as compared to the viral protein or protein complex, (v) enhanced ability to elicit a protective antibody response in an animal as compared to the viral protein or protein complex, (vi) enhanced ability to elicit production of neutralizing antibodies in an animal as compared to the viral protein or protein complex, (vii) enhanced ability to elicit production of broadly neutralizing antibodies in an animal as compared to the viral protein or protein complex, (viii) enhanced ability to elicit a protective immune response in an animal as compared to the viral protein or protein complex, and (ix) enhanced ability to bind to and elicit production of antibodies that recognize quaternary neutralizing epitopes in an animal as compared to the viral protein or protein complex. In some such embodiments the targeted cross-links are dityrosine (DT) cross-links.

In another embodiment the present invention provides a method for producing a conformationally specific vaccine immunogen, the method comprising: (a) obtaining a viral protein or protein complex in one or more conformations that favor the elicitation of protective immune responses, and (b) introducing into the viral protein or protein complex one or more cross-links that are stable under physiological conditions, wherein the engineered viral protein or protein complex has one or more of the following properties: (i) enhanced ability bind to a neutralizing antibody as compared to the viral protein or protein complex (i.e. as compared to the viral protein or protein complex without or before introduction of the cross-links), (ii) enhanced ability bind to a broadly neutralizing antibody as compared to the viral protein or protein complex, (iii) enhanced ability bind to and activate B cell receptors as compared to the viral protein or protein complex, (iv) enhanced ability to elicit an antibody response in an animal as compared to the viral protein or protein complex, (v) enhanced ability to elicit a protective antibody response in an animal as compared to the viral protein or protein complex, (vi) enhanced ability to elicit production of neutralizing antibodies in an animal as compared to the viral protein or protein complex, (vii) enhanced ability to elicit production of broadly neutralizing antibodies in an animal as compared to the viral protein or protein complex, (viii) enhanced ability to elicit a protective immune response in an animal as compared to the viral protein or protein complex, and (ix) enhanced ability to bind to and elicit production of antibodies that recognize quaternary neutralizing epitopes in an animal as compared to the viral protein or protein complex. In some such embodiments the cross-links are targeted to identified and/or selected positions within the protein or protein complex's tertiary or quaternary structure. In some such embodiments the targeted cross-links comprise dityrosine (DT) cross links.

In some embodiments where DT cross-links are used, at least one of the dityrosine cross-link originates from a point mutation of an amino acid residue to tyrosine. Furthermore, in some embodiments where DT cross-links are used, the methods described above further comprise introducing one or more point mutations to tyrosine into the viral protein or protein complex at one or more specific and/or identified regions before introducing dityrosine cross-links.

In some embodiments the methods of the invention further comprise performing an assay to assess the ability of the engineered viral protein or protein complex to bind to a neutralizing antibody, bind to a broadly neutralizing antibody, bind to and activate B cell receptors, elicit an antibody response in an animal, elicit a protective antibody response in an animal, elicit production of neutralizing antibodies in an animal, elicit production of broadly neutralizing antibodies in an animal, elicit a protective immune response in an animal, and/or elicit production of antibodies that recognize quaternary neutralizing epitopes in an animal.

In some embodiments the engineered viral proteins or protein complexes made using the methods of the invention are useful as a vaccine immunogens in animal subjects. In some embodiments the engineered viral proteins or protein complexes made using the methods of the invention are useful as a vaccine immunogens in mammalian subjects. In some embodiments the engineered viral proteins or protein complexes are useful as a vaccine immunogens in human subjects.

The methods of the present invention can be used to engineer proteins or protein complexes from numerous different viruses. In some embodiments the viral proteins or protein complexes are derived from a virus from the group consisting of Herpesvirales, Ligamenvirales, Mononegavirales, Nidovirales, Picornavirales, Lentiviruses, Human Immunodeficiency Viruses, Retroviruses, Orthomyxoviruses, Paramyxovirus, Influenza viruses, Poxviruses, Flaviviruses, Togaviruses, Coronaviruses, Rhabdoviruses, Bunyaviruses, Filoviruses, Reoviruses, Mononegavirales, Hepadnaviruses, and Hepatitis viruses. In some embodiments any viral protein may be engineered using the methods of the invention. In some embodiments the viral protein or protein complex to be engineered is a viral envelope protein or protein complex.

In some embodiments the viral proteins or protein complexes and/or the engineered viral proteins or protein complexes of the invention are soluble. In some embodiments the engineered viral proteins or protein complexes of the invention do not form aggregates, for example during the production process or when stored at a high concentration.

In some embodiments the present invention provides pharmaceutical compositions comprising the engineered viral proteins or protein complexes of the invention. In some embodiments such compositions comprise a pharmaceutically effective amount of the engineered viral proteins or protein complexes. In some embodiments such compositions also comprise a pharmaceutically acceptable carrier. In some embodiments such compositions also comprise an adjuvant.

In some embodiments, the present invention provides methods for stabilizing envelope proteins and protein complexes of pathogenic viruses to enhance their effectiveness as vaccine immunogens. In one embodiment, the present invention provides methods by which tertiary structures of proteins and/or quaternary structures of protein complexes (i.e. protein-protein interactions in a complex of two or more proteins) can be stabilized by crosslinking, whereby the crosslinks are stable under physiologically relevant conditions, do not lead to aggregate formation of the proteins or protein complexes during expression or when they are stored in high concentrations, and stabilizes the folds of the proteins or protein complexes in particular conformations that can increase the effectiveness of the proteins or protein complexes as immunogens—for example by stabilizing epitopes in such conformations that can be recognized by antibodies and/or activate B cell receptors upon binding. In some such embodiments the crosslinks can be specifically directed to particular residues within the proteins or protein complexes, such as, for example, by dityrosine bonds, or the crosslinks can be directed to amino and sulfhydryl containing amino acid side chains. In some such embodiments the crosslinks can be zero-length, or may insert additional atoms and elements into the structure of the protein. In some embodiments, the present invention provides methods by which proteins or protein complexes can be oligomerized by oligomerization motifs that can stabilize protein complexes, and also stabilize the folds of the proteins in such protein complexes in particular conformations, such as those that increase the effectiveness of the proteins or protein complexes as vaccine immunogens, for example by stabilizing epitopes in conformations that can be recognized by antibodies and activate B cell receptors upon binding.

In some embodiments the present invention provides a method for producing an engineered viral protein or protein complex useful as a vaccine immunogen, the method comprising introducing into a viral protein or protein complex one or more cross-links, thereby forming an engineered viral protein or protein complex. In some such embodiments the engineered viral protein or protein complex is useful as a vaccine immunogen in a vertebrate animal, such as in a mammal, or more specifically a human.

In some embodiments of the present invention, cross-links are introduced to stabilize the engineered viral proteins or protein complexes in a conformation that counteracts conformational masking by the virus. In some embodiments the crosslinks stabilize the engineered viral proteins or protein complexes in a conformation that can bind to and activate a B cell receptor. In some embodiments the crosslinks stabilize the engineered viral proteins or protein complexes in a conformation that is capable of eliciting an antibody response in an animal. In some embodiments the crosslinks stabilize the engineered viral proteins or protein complexes in a conformation that is capable of eliciting a neutralizing antibody response. In some embodiments the crosslinks stabilize the engineered viral proteins or protein complexes in a conformation that is capable of eliciting a broadly neutralizing antibody response. In some embodiments the crosslinks stabilize the engineered viral proteins or protein complexes in a conformation that is capable of eliciting conformationally specific antibodies. In some embodiments the crosslinks stabilize the engineered viral proteins or protein complexes in a conformation that is capable of eliciting antibodies that recognize quaternary epitopes. In some embodiments the crosslinks stabilize the engineered viral proteins or protein complexes in a conformation that is capable of eliciting antibodies that recognize quaternary neutralizing epitopes. In some embodiments the crosslinks stabilize the engineered viral proteins or protein complexes in a conformation that is capable of eliciting antibodies that recognize metastable epitopes. In some embodiments the crosslinks stabilize the engineered viral proteins or protein complexes in a conformation that is capable of eliciting a broadly protective antibody response against a virus. In some embodiments the crosslinks stabilize the engineered viral proteins or protein complexes in a conformation that is capable of eliciting a neutralizing immune response against a virus. In some embodiments the crosslinks stabilize the engineered viral proteins or protein complexes in a conformation that is capable of eliciting a broadly neutralizing immune response against a virus. In some embodiments the crosslinks stabilize the engineered viral proteins or protein complexes in a conformation that is capable of eliciting an enhanced humoral immune response in a mammal. In some embodiments the crosslinks stabilize the engineered viral proteins or protein complexes in a conformation that is capable of eliciting a humoral immune that can protect an individual from infection by a virus. In some embodiments the crosslinks stabilize the engineered viral proteins or protein complexes in a conformation that can be bound by an antibody. In some embodiments the crosslinks stabilize the engineered viral proteins or protein complexes in a conformation that can be bound by a neutralizing antibody. In some embodiments the crosslinks stabilize the engineered viral proteins or protein complexes in a conformation that can be bound by a broadly neutralizing antibody. In some embodiments the crosslinks stabilize the engineered viral proteins or protein complexes in a conformation that is thermostable. In some embodiments the crosslinks stabilize the engineered viral proteins or protein complexes in a conformation that has a prolonged shelf-life. In some embodiments the crosslinks stabilize the engineered viral proteins or protein complexes in a conformation that has a prolonged life or half-life inside the body of a subject. In some embodiments the crosslinks stabilize the engineered viral proteins or protein complexes in such a way that the conformation isomer (i.e. the form of the protein having the correct/desired conformation) has a prolonged life or half-life inside the body of a subject.

In some embodiments the engineered proteins or protein complexes of the invention can bind to and activate a B cell receptor.

In some embodiments the engineered proteins or protein complexes of the invention can elicit an antibody response in an animal, such as a neutralizing antibody response or a broadly neutralizing antibody response. In some such embodiments the antibody response comprises generation of conformationally-specific antibodies. In some such embodiments the antibody response comprises generation of antibodies that recognize quaternary epitopes, such as quaternary neutralizing epitopes or QNEs. In some such embodiments the antibody response comprises generation of antibodies that recognize metastable epitopes.

In some embodiments the engineered proteins or protein complexes of the invention can elicit a broadly protective antibody response against a virus. In some embodiments the engineered proteins or protein complexes of the invention can elicit a neutralizing immune response against a virus, such as a broadly neutralizing immune response against a virus. In some embodiments the engineered proteins or protein complexes of the invention can elicit an enhanced humoral immune response in a mammal. In some embodiments the engineered proteins or protein complexes of the invention can elicit a humoral immune response that can protect an animal subject (such as a mammalian subject, or a human subject) from infection by a virus.

In some embodiments the engineered proteins or protein complexes of the invention can bind to an antibody, such as a neutralizing antibody, or a broadly neutralizing antibody. In some embodiments the engineered proteins or protein complexes of the invention preferentially bind to neutralizing antibodies or broadly neutralizing antibodies.

In some embodiments the engineered proteins or protein complexes of the invention can bind to at least one neutralizing antibody and at least one non-neutralizing antibody, and bind to the neutralizing antibody(ies) with an affinity that is higher than that with which they bind to the non-neutralizing antibody(ies).

In some embodiments of the invention described herein, the antibodies that bind to the engineered proteins or protein complexes of the invention are monoclonal antibodies.

In some embodiments the crosslinks introduced into the engineered viral proteins or protein complexes of the invention stabilize folds in the structure of the engineered viral protein or protein complex.

In some embodiments of the present invention crosslinks are introduced into the viral proteins or protein complexes after the viral proteins or protein complexes are fully folded. In particular, in some embodiments of the present invention crosslinks are introduced into the viral proteins or protein complexes after the viral proteins or protein complexes are fully folded into a conformation that favors: (i) the elicitation of a protective immune response, or (ii) binding of a neutralizing antibody, or (iii) binding of a broadly neutralizing antibody, or (iv) binding and activation of B cell receptors, or (v) the elicitation of an antibody response in an animal, or (vi) elicitation of a protective antibody response in an animal, or (vii) elicitation of neutralizing antibodies in an animal, or (vii) elicitation of broadly neutralizing antibodies in an animal, or (viii) elicitation of a protective immune response in an animal, or (ix) elicitation of antibodies that recognize quaternary neutralizing epitopes in an animal, so as to "lock" the protein or protein complex into such a conformation.

In some embodiments the crosslinks stabilize the tertiary structure of an engineered viral protein or protein complex. In some embodiments the crosslinks stabilize the quaternary structure of an engineered viral protein complex. In some embodiments the crosslinks stabilize both the tertiary and quaternary structure of an engineered viral protein complex.

In some embodiments the engineered viral proteins or protein complexes of the invention do not form aggregates in solution. In some embodiments the engineered viral proteins or protein complexes of the invention do not form aggregates when stored in solution at high concentration.

In some embodiments the engineered viral proteins or protein complexes of the invention have cross-links that are thermostable.

In some embodiments the engineered viral proteins or protein complexes of the invention have cross-links are not toxic.

In some embodiments the engineered viral proteins or protein complexes of the invention have cross-links that are targeted cross-links, or non-targeted cross-links, or reversible cross-links, or irreversible cross-links, or crosslinks formed by use of homo-bifunctional crosslinking agents, or crosslinks formed by use of hetero-bifunctional crosslinking agents, or crosslinks formed by use of reagents that react with amine groups, or crosslinks formed by use of reagents that react with thiol groups, or crosslinks formed by use of reagents that are photoreactive, or crosslinks formed between amino acid residues, or crosslinks formed between mutated amino acid residues incorporated into the structure of the proteins or protein complexes, or oxidative crosslinks, or dityrosine bonds, or glutaraldehdye cross-links, or any combination thereof. In some embodiments the engineered viral proteins or protein complexes of the invention do not have glutaraldehyde cross-links. In some embodiments the engineered viral proteins or protein complexes of the invention do not have any disulfide bonds. In some embodiments the engineered viral proteins or protein complexes of the invention do not have any artificially introduced disulfide bonds.

In some embodiments the engineered viral proteins or protein complexes are derived from a virus from the group consisting of Herpesvirales, Ligamenvirales, Mononegavirales, Nidovirales, Picornavirales, Lentiviruses, Human Immunodeficiency Viruses, Retroviruses, Orthomyxoviruses, Paramyxovirus, Influenza viruses, Poxviruses, Flaviviruses, Togaviruses, Coronaviruses, Rhabdoviruses, Bunyaviruses, Filoviruses, Reoviruses, Mononegavirales, Hepadnaviruses, and Hepatitis viruses. In some embodiments, the engineered viral proteins or protein complexes are derived from viral envelope proteins or protein complexes. In some such embodiments the viral envelope protein or protein complex is a Type I, Type II, or Type III Fusion protein.

In some embodiments of the invention the viral proteins or protein complexes, and/or the engineered viral proteins or protein complexes, are isolated. In some embodiments of the invention the viral proteins or protein complexes, and/or the engineered viral proteins or protein complexes, are purified. In some embodiments of the invention the viral proteins or protein complexes, and/or the engineered viral proteins or protein complexes, are isolated. In some embodiments of the invention the viral proteins or protein complexes, and/or the engineered viral proteins or protein complexes, are soluble. In some embodiments of the invention the viral proteins or protein complexes, and/or the engineered viral proteins or protein complexes, are proteolytically cleaved.

In some embodiments the present invention provides methods of producing a conformationally-specific immunogen, or methods or producing an engineered viral protein or protein complex, wherein the methods comprise incorporating an engineered viral protein or protein complex into a composition, such as a pharmaceutical composition. In some such methods the pharmaceutical composition comprises a pharmaceutically effective amount of the engineered viral protein or protein complex. In some such methods the pharmaceutical composition comprises a pharmaceutically acceptable carrier. In some such methods the pharmaceutical composition comprises an adjuvant. In some such methods the pharmaceutical composition comprises a pharmaceutically effective amount of the engineered viral protein or protein complex and a pharmaceutically acceptable carrier. In some such methods the pharmaceutical composition comprises a pharmaceutically effective amount of the engineered viral protein or protein complex and a pharmaceutically acceptable carrier and an adjuvant.

In some embodiments the present invention provides compositions comprising an engineered viral protein or protein complex as described herein. In some embodiments the present invention provides pharmaceutical compositions comprising an engineered viral protein or protein complex as described herein. In some embodiments the present invention provides pharmaceutical compositions comprising a pharmaceutically effective amount of an engineered viral protein or protein complex as described herein. In some embodiments the present invention provides pharmaceutical compositions comprising a an engineered viral protein or protein complex as described herein and a pharmaceutically acceptable carrier. In some embodiments the present invention provides pharmaceutical compositions comprising a an engineered viral protein or protein complex as described herein and an adjuvant. In some embodiments the present invention provides pharmaceutical compositions comprising a pharmaceutically effective amount of an engineered viral protein or protein complex as described herein and a pharmaceutically acceptable carrier. In some embodiments the present invention provides pharmaceutical compositions comprising a pharmaceutically effective amount of an engineered viral protein or protein complex as described herein, a pharmaceutically acceptable carrier, and an adjuvant.

In some embodiments the present invention provides engineered viral proteins or protein complexes, or compositions comprising engineered viral proteins or protein complexes, wherein the engineered viral proteins or protein complexes have one or more of properties selected from the group consisting of: (i) enhanced ability bind to a neutralizing antibody, (ii) enhanced ability bind to a broadly neutralizing antibody, (iii) enhanced ability bind to and activate B cell receptors, (iv) enhanced ability to elicit an antibody response in an animal, (v) enhanced ability to elicit a protective antibody response in an animal, (vi) enhanced ability to elicit production of neutralizing antibodies in an animal, (vii) enhanced ability to elicit production of broadly neutralizing antibodies in an animal, (viii) enhanced ability to elicit a protective immune response in an animal, and (ix) enhanced ability to elicit production of antibodies that recognize quaternary neutralizing epitopes in an animal.

In some embodiments the present invention provides methods of producing a conformationally-specific vaccine immunogen, or methods of producing an engineered viral protein or protein complex, wherein the methods comprise performing an assay to assess the ability of the engineered viral protein or protein complex to bind to a neutralizing antibody, bind to a broadly neutralizing antibody, bind to and activate B cell receptors, elicit an antibody response in an animal, elicit a protective antibody response in an animal, elicit production of neutralizing antibodies in an animal, elicit production of broadly neutralizing antibodies in an animal, elicit a protective immune response in an animal, and/or elicit production of antibodies that recognize quaternary neutralizing epitopes in an animal.

As used herein the terms "protein" and "polypeptide" are used interchangeably, unless otherwise stated. As used herein the term "protein complex" refers to an assembly of two or more proteins. Unless otherwise stated, all description herein that relates to proteins applies equally to protein complexes, and vice versa. As used herein the term "engineered" in relation to proteins and/or protein complexes generally refers to those that include cross-links, typically as the result of the introduction of cross-links in order to stabilize the protein or protein complex in a desirable conformation. Unless otherwise stated, all description herein that relates to proteins or protein complexes (including, but not limited to, that related to methods of making and using such proteins), relates equally to engineered proteins/protein complexes and non-engineered proteins/protein complexes (e.g. those with no cross-links added or before addition of cross-links) and to all homologs, orthologs, analogs, derivatives, mutant forms, fragments, chimeras, fusion proteins etc. thereof. The terms "protein" and "protein complex" include naturally occurring viral proteins and protein complexes, and viral proteins and protein complexes that have been altered in some way, such as by recombinant means, chemical means, or any other means. Such proteins and protein complexes include, but are not limited to, those from viruses that are pathogenic, such as those that are pathogenic to humans or other animals, and for which it is desirable to engineer such proteins and protein complexes, for example in order to enhance the immunogenicity of the protein or protein complex and/or to enhance the capability of the protein or protein complex to elicit a humoral immune responses in an animal, such as a human or other mammal.

In some embodiments the methods and compositions of the invention can be used with any suitable viral protein or protein complex. In some embodiments the viral proteins and protein complexes are viral envelope proteins or protein complexes. Many viruses have a viral envelope covering their protein capsid. The envelope of such viruses typically comprises host cell phospholipids and proteins, and further includes viral proteins and/or protein complexes—which typically comprise glycoproteins. The viral envelope mediates many of the processes involved in viral entry into host cells and infection. For example, surface viral envelope glycoproteins of a virus particle can bind to host cell receptor molecules on the host cell's membrane and affect fusion of the viral envelope with the host cell's membrane allowing subsequent entry of the capsid and viral genome and infection of the host cell. Because viral envelope proteins are on the surface of viral particles, and are therefore accessible, they are considered among the best targets for vaccine immunogen design and development.

Viral proteins and/or protein complexes used in accordance with the present invention can have, or can be derived from, the nucleotide and/or amino acid sequences of any suitable virus proteins or protein complexes known in the art, and can have, or be derived from nucleotide and/or amino acid sequences that have at least about 85%, or about 90%, or about 95%, or about 98% sequence identity to any such known sequences, or to any groups, subgroups, families, subfamilies, types, subtypes, genera, species, strains, and clades, etc. of any known viruses. As used in the present specification the terms "about" and "approximately," when used in relation to numerical values, mean within + or −20% of the stated value.

In some embodiments, the invention provides fragments of the proteins or protein complexes of the invention, such as those comprising, consisting essentially of, or consisting of at least about 10 amino acids, 20 amino acids, 50 amino acids, 100 amino acids, 200 amino acids, 500 amino acids, 1000 amino acids, 2000 amino acids, or 5000 amino acids.

Derivatives or analogs of the proteins of the invention include those molecules comprising regions that are substantially homologous to a protein or fragment thereof (e.g., in various embodiments, those having at least about 40% or 50% or 60% or 70% or 80% or 90% or 95% identity with an amino acid or nucleic acid sequence of the invention when aligned using any suitable method known to one of ordinary skill in the art, such as, for example, using a computer homology program known in the art) or whose encoding nucleic acid is capable of hybridizing to a coding nucleic acid sequence of a protein of the invention, under high stringency, moderate stringency, or low stringency conditions.

In some embodiments one or more amino acid residues within a protein or protein complex can be substituted with another amino acid. For example, one or more amino acid residues can be substituted by another amino acid having a similar polarity and that may acts as a functional equivalent, resulting in a silent alteration. In some embodiments substitutions for an amino acid within the sequence may be selected from other members of the class to which the amino acid belongs e.g. to create a conservative substitution. For example, the nonpolar (hydrophobic) amino acids include alanine, leucine, isoleucine, valine, proline, phenylalanine, tryptophane and methionine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid. Such substitutions are generally understood to be conservative substitutions.

Proteins and protein complexes can be produced by any methods known to one of ordinary skill in the art, and manipulations of such proteins or protein complexes can occur or be made at the nucleic acid or protein/amino acid level. For example, a cloned nucleotide sequence encoding a protein or protein complex can be modified by any of numerous strategies known to one of ordinary skill in the art.

Chimeric proteins can be made by any method known to one of ordinary skill in the art, and may comprise, for example, one or several proteins of the invention, such as those that have been engineered enhance their immunogenicit, and/or any fragment, derivative, or analog thereof (preferably consisting of at least a domain of a polypeptide, protein, or protein complex to be engineered, or at least 6, and preferably at least 10 amino acids of the protein) joined at its amino- or carboxy-terminus via a peptide bond to an amino acid sequence of a different protein. In some embodiments such chimeric proteins can be produced by any method known to one of ordinary skill in the art, including, but not limited to, recombinant expression of a nucleic acid encoding a chimeric protein (e.g. comprising a first coding sequence joined in-frame to a second coding sequence); ligating the appropriate nucleic acid sequences encoding the desired amino acid sequences to each other in the proper coding frame, and expressing the chimeric product. In another embodiment protein synthetic techniques can be used to generate any protein (including chimeric protein), for example by use of a peptide synthesizer.

In some embodiments viral proteins and/or protein complexes can be engineered in such a way that they are capable of eliciting a humoral immune responses that may protect, or help protect, an individual from infection by a particular virus. The phrase "capable of eliciting a humoral immune response," as used herein, can refer, in some embodiments, to a protein or protein complex that can cause cells of the immune system to produce antibodies that bind to the proteins or complexes. In some embodiments the antibodies bind with dissociation constants (KD) of less than $5 \times 10^{-2}$ M, $10^{-2}$ M, $5 \times 10^{-3}$ M, $10^{-3}$ M, $5 \times 10^{-4}$ M, $10^{-4}$ M, $5 \times 10^{-5}$ M, $10^{-5}$ M, $5 \times 10^{-6}$ M, $10^{-6}$ M, $5 \times 10^{-7}$ M, $10^{-7}$ M, $5 \times 10^{-8}$ M or $10^{-8}$ M, $5 \times 10^{-9}$ M, $10^{-9}$ M, $5 \times 10^{-10}$ M, $10^{-10}$ M, $5 \times 10^{-11}$ M, $10^{-11}$ M, $5 \times 10^{-12}$ M, $10^{-12}$ M, $5 \times 10^{-13}$ M, $10^{-13}$ M, $5 \times 10^{-14}$ M, $10^{-14}$ M, $5 \times 10^{-15}$ M, or $10^{-15}$ M, with an off rate ($k_{off}$) of less than or equal to $5 \times 10^{-2}$ sec$^{-1}$, $10^{-2}$ sec$^{-1}$, $5 \times 10^{-3}$ sec$^{-1}$, $10^{-3}$ sec$^{-1}$, $5 \times 10^{-4}$ sec$^{-1}$, $10^{-4}$ sec$^{-1}$, $5 \times 10^{-5}$ sec$^{-1}$, $10^{-5}$ sec$^{-1}$, or $10^{-5}$ sec$^{-1}$, $5 \times 10^{-6}$ sec$^{-1}$, $10^{-6}$ sec$^{-1}$, $5 \times 10^{-7}$ sec$^{-1}$, or $10^{-7}$ sec$^{-1}$, and/or with an on rate ($k_{on}$) of greater than or equal to $10^{3}$ M$^{-1}$ sec$^{-1}$, $5 \times 10^{3}$ M$^{-1}$ sec$^{-1}$, $10^{4}$ M$^{-1}$ sec$^{-1}$, $5 \times 10^{4}$ M$^{-1}$ sec$^{-1}$, $10^{5}$ M$^{-1}$ sec$^{-1}$, $5 \times 10^{5}$ M$^{-1}$ sec$^{-1}$, $10^{6}$ M$^{-1}$ sec$^{-1}$, or $5 \times 10^{6}$ M$^{-1}$ sec$^{-1}$, or $10^{7}$ M$_{-1}$ sec$_{-1}$.

Proteins and protein complexes may also be altered by adding or deleting amino acid residues, by adding or removing post-translational modifications, by adding or removing chemical modifications or appendixes, and/or by introducing any other mutations or modifications known to those of ordinary skill in the art.

Included within the scope of the invention are proteins and protein complexes that are modified during or after translation or synthesis, for example, by crosslinking, glycosylation, acetylation, phosphorylation, amidation, derivatization by known protecting/blocking groups, proteolytic cleavage, or buy any other means known in the art. For example, in some embodiments the proteins and protein complexes may be subjected to chemical cleavage by cyanogen bromide, trypsin, chymotrypsin, papain, V8 protease, NaBH4, acetylation, formylation, oxidation, reduction, metabolic synthesis in the presence of tunicamycin, etc.

The proteins and protein complexes of the invention can be made by any suitable means known in the art, including recombinant means and chemical synthesis means. In addition, proteins and protein complexes of the invention can be engineered for enhanced immunogenicity using any suitable means known in the art. For example, a peptide corresponding to a portion of a protein or protein complex can be synthesized by use of a peptide synthesizer. Furthermore, if desired, artificial, synthetic, or non-classical amino acids or chemical amino acid analogs can be used to make the proteins and protein complexes of the invention or introduced into the proteins and protein complexes of the invention. Non-classical amino acids include, but are not limited to, the D-isomers of the common amino acids, fluoro-amino acids, and "designer" amino acids such as β-methyl amino acids, Cγ-methyl amino acids, Nγ-methyl amino acids, and amino acid analogs in general. Additional non-limiting examples of non-classical amino acids include, but are not limited to: α-aminocaprylic acid, Acpa; (S)-2-aminoethyl-L-cysteine/HCl, Aecys; aminophenylacetate, Afa; 6-amino hexanoic acid, Ahx; γ-amino isobutyric acid and α-aminoisobytyric acid, Aiba; alloisoleucine, Aile; L-allylglycine, Alg; 2-amino butyric acid, 4-aminobutyric acid, and α-aminobutyric acid, Aba; p-aminophenylalanine, Aphe; b-alanine, Bal; p-bromophenylalaine, Brphe; cyclohexylalanine, Cha; citrulline, Cit; β-chloroalanine, Clala; cycloleucine, Cle; p-cholorphenylalanine, Clphe; cysteic acid, Cya; 2,4-diaminobutyric acid, Dab; 3-amino propionic acid and 2,3-diaminopropionic acid, Dap; 3,4-dehydroproline, Dhp; 3,4-dihydroxylphenylalanine, Dhphe; p-flurophenylalanine, Fphe; D-glucoseaminic acid, Gaa; homoarginine, Hag; δ-hydroxylysine/HCl, Hlys; DL-β-hydroxynorvaline, Hnvl; homoglutamine, Hog; homophenylalanine, Hoph; homoserine, Hos; hydroxyproline, Hpr; p-iodophenylalanine, Iphe; isoserine, Ise; α-methylleucine, Mle; DL-methionine-S-methylsulfoniumchloide, Msmet; 3-(1-naphthyl) alanine, 1Nala; 3-(2-naphthyl) alanine, 2Nala; norleucine, Nle; N-methylalanine, Nmala; Norvaline, Nva; O-benzylserine, Obser; O-benzyltyrosine, Obtyr; O-ethyltyrosine, Oetyr; O-methylserine, Omser; O-methylthreonine, Omthr; O-methyltyrosine, Omtyr; Ornithine, Orn; phenylglycine; penicillamine, Pen; pyroglutamic acid, Pga; pipecolic acid, Pip; sarcosine, Sar; t-butylglycine; t-butylalanine; 3,3,3- trifluroalanine, Tfa; 6-hydroxydopa, Thphe; L-vinylglycine, Vig; (−)-(2R)-2-amino-3-(2-aminoethylsulfonyl) propanoic acid dihydroxochloride, Aaspa; (2S)-2-amino-9-hydroxy-4,7-dioxanonanoic acid, Ahdna; (2S)-2-amino-6-hydroxy-4-oxahexanoic acid, Ahoha; (−)-(2R)-2-amino-3-(2-hydroxy-ethylsulfonyl) propanoic acid, Ahsopa; (−)-(2R)-2-amino-3-(2-hydroxyethylsulfanyl) propanoic acid, Ahspa; (2S)-2-amino-12-hydroxy-4,7,10-trioxadodecanoic acid, Ahtda; (2S)-2,9-diamino-4,7-dioxanonanoic acid, Dadna; (2S)-2,12-diamino-4,7,10-trioxadodecanoic acid, Datda; (S)-5,5-difluoronorleucine, Dfnl; (S)-4,4-difluoronorvaline, Dfnv; (3R)-1-1-dioxo-[1,4]thiaziane-3-carboxylic acid, Dtca; (S)-4,4,5,5,6,6,6-heptafluoronorleucine, Hfnl; (S)-5,5,6,6,6-pentafluoronorleucine, Pfnl; (S)-4,4,5,5,5-pentafluoronorvaline, Pfnv; and (3R)-1,4-thiazinane-3-carboxylic acid, Tca. Furthermore, the amino acid can be D (dextrorotary) or L (levorotary). For a review of classical and non-classical amino acids, see Sandberg et al., 1998 (Sandberg et al., 1998. New chemical descriptors relevant for the design of biologically active peptides. A multivariate characterization of 87 amino acids. J Med Chem 41(14): pp. 2481-91).

Any suitable method known in the art may be used to generate or obtain proteins and protein complexes according to the present invention. Similarly, the proteins and protein complexes of the invention may be isolated or purified using any suitable method known in the art. Such methods include, but are not limited to, chromatography (e.g. ion exchange, affinity, and/or sizing column chromatography), ammonium sulfate precipitation, centrifugation, differential solubility, or by any other technique for the purification of proteins known to one of ordinary skill in the art. The proteins and protein complexes may be purified from any source that produces such proteins/complexes. For example, proteins and protein complexes may be purified from sources including, prokaryotic, eukaryotic, mono-cellular, multi-cellular, animal, plant, fungus, vertebrate, mammalian, human, porcine, bovine, feline, equine, canine, avian, tissue culture cells, and any other source. The degree of purity may vary, but in various embodiments, the purified protein is provided in a form in which is it comprises more than about 10%, 20%, 50%, 75%, 85%, 95%, 99%, or 99.9% of the total protein.

In some embodiments point mutations can be introduced into proteins and/or protein complexes to stabilize particular conformations. In some embodiments proteins may be deglycosylated, dephosphorylated, or otherwise chemically or enzymatically treated/altered to render them more immunogenic, and capable of generating neutralizing and broadly neutralizing immune responses against viral epitopes.

In embodiments where mutations are introduced into a protein or protein complex, the protein(s) can be micro-sequenced to determine a partial amino acid sequence. In some embodiments the partial amino acid sequence can then be used together with, for example, library screening and recombinant nucleic acid methods known in the art, for example to isolate clones having, or for introduction of, desired mutations.

In some embodiments the proteins and protein complexes of the invention may be isolated and purified from other proteins, or any other undesirable products, by standard methods including, but not limited to, chromatography (e.g., sizing column chromatography, glycerol gradients, affinity), centrifugation, or by any other standard technique for the purification of proteins. In specific embodiments it may be necessary to separate proteins that are not part of one or more stabilized proteins or protein complexes of the invention (e.g. that were not cross-linked), but that may, for example, homo- or heterodimerize with other proteins. Such separation may be achieved by any means known in the art, including, but not limited to, separation methods that use detergents and/or reducing agents.

The yield of engineered proteins and protein complexes of the invention can be determined by any means known in the art, for example, by comparing the amount of engineered proteins and/or protein complexes produced as compared to the amount of the starting material (i.e. the non-engineered proteins or protein complexes). Protein concentrations are determined by standard procedures, such as, for example, Bradford or Lowrie protein assays. The Bradford assay is compatible with reducing agents and denaturing agents (Bradford, M, 1976. Anal. Biochem. 72: 248). The Lowry assay has better compatibility with detergents and the reaction is more linear with respect to protein concentrations and read-out (Lowry, O J, 1951. Biol. Chem. 193: 265).

In some embodiments proteins and/or protein complexes are obtained and/or isolated in a conformation that favors the elicitation of a protective immune response, and are subsequently cross-linked in order to stabilize such conformation. Proteins and/or protein complexes may be obtained and/or isolated in conformations that favor the elicitation of a protective immune response by any suitable method known in the art, including, for example, but not limited to, standard protein purification methods, such as ion exchange and size exclusion chromatography, and affinity chromatography. As further non-limiting examples, proteins and protein complexes to be isolated may be expressed in the presence of, or co-expressed with, binding compounds, peptides, or proteins that stabilize the conformation of the proteins and protein complexes to be isolated when so bound. As further non-limiting examples, proteins and protein complexes to be isolated may be expressed in high or low ionic media, or isolated in high or low ionic buffers or solutions by the methods described herein. Proteins and protein complexes to be isolated may also be isolated at one or more temperatures that favor preservation of the desired conformation. Proteins and protein complexes may also be isolated over a period of time that diminishes the degree to which a preparation would have lost the desired conformation. The degree to which a preparation of proteins or protein complexes retains one or more conformations that favor the elicitation of protective immune responses may be assayed by any suitable method known in the art, including, for example, but not limited to, biochemical, biophysical, immunologic, and virologic analyses. Such assays include, for example, but are not limited to, immunoprecipation, ELISA, or Enzyme-linked immunosorbent spot (ELISPOT) assays to analyze, for example, binding to protective or neutralizing or broadly neutralizing antibodies or binding proteins; binding to non-protective, non-neutralizing, or weakly protective or neutralizing antibodies or binding proteins; crystallographic analysis, including co-crystallization with antibodies, sedimentation, analytical ultracentrifugation, dynamic light scattering (DLS), electron microscopy (EM), cryo-EM tomography, calorimetry, surface plasmon resonance (SPR), fluorescence resonance energy transfer (FRET), circular dichroism analysis, and small angle x-ray scattering; neutralization assays of immune sera following immunization with proteins or protein complexes; antibody-dependent cellular cytotoxicity assays of immune sera following immunization with proteins or protein complexes; and virologic challenge studies in animals, and passive transfer assays.

Proteins and/or protein complexes of the invention may be stabilized by intra- and/or intermolecular crosslinking. Intramolecular crosslinking may stabilize the folds of particular protein conformations, and intermolecular crosslinking may stabilize both protein-protein interactions and the folds of particular protein conformations, such as those in which the proteins and protein complexes of the present invention have the desired immunogenic properties.

Crosslinks may include, but are not limited to, reversible crosslinks resulting from the use of homo- and heterobifunctional crosslinking agents that react with amine and/or thiol groups, photoreactive crosslink reagents, any crosslinks that may form between non-classical amino acids incorporated into the structure of a protein or protein complex, and any oxidative crosslinks, such as, but not limited to, dityrosine cross-links/bonds. Irreversible crosslinks, as used in the context of this application, include those that are not dissolved under physiologically relevant conditions, and do not lead to aggregate formation during expression or when stored in high concentrations. Disulfide bonds are not irreversible cross-links. Rather they are reversible crosslinks and may dissolve under physiologically relevant conditions and/or lead to aggregate formation during protein expression and/or production or when stored in high concentrations.

The crosslinks may be targeted to specific sites in the structure of proteins and/or protein complexes in order to achieve the desired immunogenic properties. Alternatively, proteins an protein complexes with the desired crosslinks may be isolated from a mixture of crosslinked and uncrosslinked proteins with and without the desired modifications, for example based on chemical, physical, and/or functional characteristics. Such characteristics may include, for example, molecular weight, molecular volume, any and all chromatographic properties, mobility in any all forms of electrophoresis, and any and all antigenic and biochemical characteristics, fluorescence and any and all other biophysical characteristics, solubility in aqueous solutions, (organic) solvents, and/or hybrid solutions in the presence or absence of other molecules in solution (e.g. ions) at different concentrations, affinity to mono- and/or polyclonal antibodies, affinity to receptors, other proteins, DNA, RNA, lipids, other bio- and non-bio-organic molecules and complexes, inorganic molecules and complexes, ions, any and all structural characteristics, enzymatic, immunological, tissue culture, diagnostic, pharmaceutical, and any other activity or activities, and any other characteristics that are known to one of ordinary skill in the art.

A wide variety of methods of crosslinking proteins intra- and inter-molecularly are known in the art, including those having cross-links with varying lengths of spacer arms, and those with and without fluorescent and functional groups for purification. Such methods include, but are not limited to, the use of heterobifunctional crosslinkers (e.g. succinimidyl acetylthioacetate (SATA), trans-4-(maleimidylmethyl)cyclohexane-1-carboxylate (SMCC), and succinimidyl 3-(2-pyridyldithio)propionate (SPDP)), homobifunctional crosslinkers (e.g. succinimidyl 3-(2-pyridyldithio)propionate), photoreactive crosslinkers (e.g. 4-azido-2,3,5,6-tetrafluorobenzoic acid, STP ester, sodium salt (ATFB, STP ester), 4-azido-2,3,5,6-tetrafluorobenzoic acid, succinimidyl ester (ATFB, SE), 4-azido-2,3,5,6-tetrafluorobenzyl amine, hydrochloride, benzophenone-4-isothiocyanate, benzophenone-4-maleimide, 4-benzoylbenzoic acid, succinimidyl ester, N-((2-pyridyldithio)ethyl)-4-azidosalicylamide (PEAS; AET), thiol reactive crosslinkers (e.g. maleimides and iodoacetamides), amine reactive crosslinkers (e.g. glutaraldyde, bis(imido esters), bis(succinimidyl esters), diisocyanates and diacid chlorides). Because thiol groups are highly reactive and relatively rare in most proteins by comparison to amine groups, thiol-reactive crosslinking may be used in some embodiments. In cases where thiol groups are missing or not present at appropriate sites in the structures of proteins and protein complexes, they can be introduced using one of several thiolation methods. For examples, Succinimidyl trans-4-(maleimidylmethyl)cyclohexane-1-carboxylate can be used to introduce thiol-reactive groups at amine sites.

Several oxidative crosslinks are known, such as disulfide bonds (which form spontaneously and are pH and redox sensitive), and dityrosine bonds (which are highly stable, and irreversible under physiological conditions).

Therapeutic proteins are generally complex, heterogeneous, and subject to a variety of enzymatic or chemical modifications during expression, purification, and long-term storage. Because they are often lyophilized or stored and administered to patients at relatively high concentrations, aggregate formation is often a problem, as it reduces manufacturing yields and denatures the structure of the complex so that humoral immune responses to conformationally masked epitopes are less likely to yield broadly neutralizing antibodies.

Engineering cystine side-chains by point mutation to positions where disulfide bonds will form stabilizes the HIV gp120 and gp41 proteins, and fragments thereof have been stabilized for the purpose of developing an immunogen capable of eliciting broadly neutralizing and/or broadly neutralizing humoral immune responses (Beddows et al., 2006. Construction and Characterization of Soluble, Cleaved, and Stabilized Trimeric Env Proteins Based on HIV Type I Env Subtype A. AIDS Res Hum Retroviruses 22(6): 569-579; Farzan et al., 1998. Stabilization of Human Immunodeficiency Virus Type 1 Envelope Glycoprotein Trimers by Disulfide Bonds Introduced into the gp41 Glycoprotein Ectodomain. J Virol 72(9): 7620-25). Disulfide bonds are, however, known to be pH sensitive and to be dissolved under certain redox conditions, and the preventative and/or therapeutic utility of proteins and/or protein complexes engineered with disulfide crosslinks, for example to be used as immunogens in vivo, may therefore be compromised. Furthermore, undesired disulfide bonds often form between proteins with free sulfhydryl groups that mediate aggregate formation (see, for example, Harris R J et al. 2004, Commercial manufacturing scale formulation and analytical characterization of therapeutic recombinant antibodies. Drug Dev Res 61 (3): 137-154; Costantino & Pikal (Eds.), 2004. Lyophilization of Biopharmaceuticals, editors Costantino & Pekal. Lyophilization of Biopharmaceuticals. Series: Biotechnology: Pharmaceutical Aspects II, see pages 453-454; Tracy et al., 2002, U.S. Pat. No. 6,465,425), which has also been reported as a problem with HIV gp120 and gp41 (Jeffs et al. 2004. Expression and characterisation of recombinant oligomeric envelope glycoproteins derived from primary isolates of HIV-1. Vaccine 22:1032-1046; Schulke et al., 2002. Oligomeric and conformational properties of a proteolytically mature, disulfide-stabilized human immunodeficiency virus type 1 gp140 envelope glycoprotein. J Virol 76:7760-7776).

An alternative means of cross-linking proteins involves the formation of dityrosine (DT) bonds. Dityrosine cross-linking introduces one or more covalent carbon-carbon bonds into proteins or protein complexes. This provides a method for stabilizing proteins, protein complexes, and conformations, by introduction of intra- and/or inter-polypeptide di-tyrosine bonds while maintaining their structural and functional integrity (Marshall et al., U.S. Pat. Nos. 7,037,894 & 7,445,912). Creating covalent bonds at specific, targeted locations within proteins can reinforce particular 3D-arrangements of the protein structure and can provide a high degree of stabilization.

The minimally altering, and zero-length DT crosslink is not hydrolyzed under physiological conditions, and has been demonstrated to maintain proteins' structural integrity by liquid chromatography/mass spectrometry (LC/MS). Dityrosine crosslinks are known to be safe, as they form naturally in vivo, both in the context of proteins evolved to utililze their specific characteristics (e.g. Elvin C M et al. 2005, Nature 437:999-1002; Tenovuo J & Paunio K 1979, Arch Oral Biol.; 24(8):591-4), and as a consequence of non-specific protein oxidation (Giulivi et al. 2003, Amino Acids 25(3-4):227-32), and as they are present in large quantities in some of our most common foods: DT bonds form the structure of wheat gluten—the quarternary protein structure comprising the glutenin subunits—e.g. in bread dough during mixing and baking (Tilley et al. 2001, Agric. Food Chem 49, 2627).

Dityrosine bonds do not form spontaneously in vitro. Rather, the enzymatic crosslink reaction is carried out under optimized conditions to preserve protein structure and function. Therefore, non-specific bonding/aggregation does not occur (as compared to free-sulfhydryl groups), and therefore large-scale manufacturing of a DT stabilized immunogen may be economically more feasible.

Tyrosyl side-chains are present in many redox enzymes, and catalysis of the enzyme-specific reactions often involves tyrosyl radicals that are long-lived and have comparatively low reactivity. Under optimized conditions radical formation is specific to tyrosyl side-chains. In close proximity to each tyrosyl side chains undergo radical coupling and form a covalent, carbon-carbon bond. Tyrosyl radicals that do not react revert to non-radicalized tyrosyl side-chains (Malencik & Anderson, 2003. Dityrosine as a product of oxidative stress and fluorescent probe. Amino Acids 25: 233-247). Therefore, tyrosyl side-chains must be situated in close proximity to form DT bonds, either within a single folded polypeptide chain, or on closely interacting protein domains within a complex. Because a Cα-Cα separation of approximately 5-8 Å is prerequisite to bond formation (Brown et al., 1998. Determining protein-protein interactions by oxidative cross-linking of a glycine-glycine-histidine fusion protein. Biochemistry 37, 4397-4406; Marshall et al. 2006, U.S. Pat. No. 7,037,894), and because no atom is added in the formation of these bonds, the resulting "staple" can be targeted to be non-disruptive to the protein structure. These tyrosines may be present in the primary structure of the protein or added by controlled point mutation.

The major advantages of dityrosine crosslinking in protein engineering include (i) the ability to target specific residues for crosslinking (based on the primary, secondary, tertiary, and/or quaternary structures of proteins and complexes), (ii) minimal structural modification, (iii) specificity of the reaction (tyrosine is the only amino acid known to form crosslinks under specific crosslinking conditions; proteins remain otherwise intact); (iv) stability of the linkage, (v) zero length crosslink (no atom added), and (vi) scalable chemistry.

In some embodiments dityrosine ("DT") bonds/crosslinks may be targeted to specific residue pairs within the structure of a protein or protein complex where DT bonds will, or are predicted to, form, due to, for example, their close proximity. This may either be done with proteins in which, at the targeted residue pair(s) tyrosyl sidechains are already present, and other tyrosyl side chains will not, or are not predicted to, form DT bonds because, for example, they are not in close enough proximity to each other. Proteins/protein complexes can also be engineered in such a way that at the targeted residue pair(s), tyrosyl sidechains are present, and at residues where it may be undesirable for DT crosslinks to form, at least one of the tyrosyl side chains is replaced with another side chain, such as a phenylalanine side chain (see, for example, Marshall C P et al., U.S. patent application Ser. No. 09/837,235, the contents of which are hereby incorporated by reference). This may be achieved, for example, by introducing point mutations to tyrosine or from tyrosine in the nucleic acid sequences directing the expression of the proteins or protein complexes using any suitable methods known in the art. Alternatively, the proteins/protein complexes may be synthesized, purified, and/or produced by any suitable methods known in the art to include desirable tyrosine residues and remove undesirable tyrosine residues.

In order to form DT bonds, proteins with tyrosyl side chains at the targeted residue pair(s) can be subjected to reaction conditions that lead to the formation of DT bonds. Such conditions are, or become, oxidative reaction conditions, as the DT bond formation reaction is an oxidative crosslink. In some embodiments the DT cross-linking reaction conditions yield proteins that are otherwise not, or not detectably, modified. Such conditions may be obtained by use of enzymes that catalyze the formation of $H_2O_2$, such as peroxidases. DT bond formation may be monitored by spectrophotometry with an excitation wavelength of 320 nm, and fluorescence measured at a wavelength of 400 nm, while loss of tyrosyl fluorescence is monitored also monitored by standard procedures. When loss of tyrosyl florescence is no longer stoicometric with DT bond formation, the reaction may be stopped by any methods known to one skilled in the art, such as, for example, by the addition of a reducing agent and subsequent cooling (on ice) or freezing of the sample.

Proteins can also be stabilized using heterologous oligomerization motifs, such as timerization motifs. Stabilizing oligomeric protein complexes by means of evolutionarily developed motifs in nature can be accomplished by engineering heterologous oliomerization motifs into the structure of the polpeptides of the complex.

Where viral proteins form trimers that would be more immunogenic if trimerization were stabilized in particular conformations, heterologous trimererization motifs can be used to substitute the protein-protein interaction domains that mediate trimerization of the wild type viral proteins, and that fit the overall structural confinements/constraints of the viral protein complex. There are a wide variety of trimerization domains in natural proteins that can be used for these purposes such as, for example, but not limited to, those described in Habazettl et al., 2009 (Habazettl et al., 2009. NMR Structure of a Monomeric Intermediate on the Evolutionarily Optimized Assembly Pathway of a Small Trimerization Domain. J. Mol. Biol. pp. null), Kammerer et al., 2005. (Kammerer et al., 2005. A conserved trimerization motif controls the topology of short coiled coils. Proc Natl Acad Sci USA 102 (39): 13891-13896), Innamorati et al., 2006. (Innamorati et al., 2006. An intracellular role for the C1q-globular domain. Cell signal 18(6): 761-770), and Schelling et al., 2007 (Schelling et al., 2007. The reovirus σ-1 aspartic acid sandwich: A trimerization motif poised for conformational change. Biol Chem 282(15): 11582-11589)

Stabilizing trimeric protein complexes can also be accomplished using the GCN4 and T4 fibrinitin motifs (Pancera et al., 2005. Soluble Mimetics of Human Immunodeficiency Virus Type 1 Viral Spikes Produced by Replacement of the Native Trimerization Domain with a Heterologous Trimerization Motif: Characterization and Ligand Binding Analysis. J Virol 79(15): 9954-9969; Guthe et al., 2004. Very fast folding and association of a trimerization domain from bacteriophage T4 fibritin. J. Mol. Biol. v337 pp. 905-15; Papanikolopoulou et al., 2008. Creation of hybrid nanorods from sequences of natural trimeric fibrous proteins using the fibritin trimerization motif. Methods Mol Biol 474:15-33).

Heterologous oligomerization motifs may be introduced by any recombinant methods known to one of ordinary skill in the art in order to stabilize the protein-protein interactions of proteins and protein complexes of present invention. Such heterologous oligomerization motifs should fit the structural confinements/constraints of the protein/protein complex, and are likely to yield best results when introduced in such a way that the overstructure of the protein/protein complex is otherwise not distorted. Heterologous oligomerization domains are therefore preferably introduced in their most reduced form/structure, and may be introduced in the presence or absence of additional linkers/spacers known to one of ordinary skill in the art that may minimize distortion of the overall protein complex structure If the structure and/or immunogenicity of a polypeptide complex is compromised or altered by a cross-link reaction, maintaining its overall structure and function can be achieved by controlling the availability of amino acid side-chains for the cross-linking reaction. For example, tyrosyl side-chains that are available for the reaction, but that lead to the distortion of the structure of the complex, and that compromise the immunogenicity/antigenicity of the complex, can be removed by mutating such residues to another amino acid such as, for example, phenylalanine. Furthermore, point mutations may be introduced at positions where the amino acid side-chains will react with crosslinking agents or each other, such that the formation of the bond(s) causes the most beneficial outcome. These positions may also be identified as described herein.

To achieve a stabilized protein or protein complex with enhanced immunogenicity, positions within each protein can be identified at which a reactive side-chain would be able to form a bond with a reactive side-chain elsewhere on the protein/complex. Such positions can be selected both with respect toward maintaining or improving upon the immunogenicity/antigenicity of the protein/complex, and with respect toward the suitability of the other position involved in the bond. The positions to be cross-linked may therefore selected in pairs.

When at a selected residue a reactive side-chain is not already present, a point mutation may be introduced, for example using molecular biological methods to introduce such a point mutation into the cDNA of a nucleic acid directing its expression, such that a reactive side-chain is present and available for the reaction.

Several strategies may be used to target cross-links to specific locations in a protein or protein complex. Any method known to one skilled in the art may be used to identify residue pairs of a polypeptide, protein, or protein complex that, when crosslinked, could provide a protein or protein complex that is capable of generating a neutralizing response against a viral epitope, and that may lead to the production of neutralizing antibodies in vertebrates, mammals, or preferably humans. Such methods may be based on the selection processes described in Marshall et al. (U.S. Pat. Nos. 7,037,894 and 7,445,912, the contents of which are hereby incorporated by reference), whereby stabilization of the protein or protein complex may improve upon its immunogenic properties. Any computational methods known to one of ordinary skill in the art may also be used to identify positions at which crosslinks could stabilize interactions between regions of the secondary, tertiary, or quaternary structure of a protein or protein complex. Furthermore, screening/scanning of residue pairs by any methods known to one of ordinary skill in the art may be used to identify positions at which the crosslink(s) for in the polypeptides, proteins, or protein complexes of the present invention and provide(s) them the capability of generating neutralizing or broadly neutralizing immune responses advantages of the present invention. Any other methods known to one of ordinary skill in the art may be used, including for example, the use of data matagenic analyses (for example, but not limited to, alanine screening).

Where proteins or protein complexes of the present invention are cross-linked for the purpose of stabilizing one or more particular conformations of a protein, or for the purpose of stabilizing protein-protein interactions in a protein complex, the chemical modifications may be applied by standard methods known to one of ordinary skill in the art, for example after a protein is prepared, expressed, and/or purified. Any one, or a combination of, the targeting strategies and cross-linking strategies described herein, or known in the art, may be used. Alternatively, the modification may not be targeted, and proteins with the desired modifications, activities, and/or specificities may be isolated from a mixture of modified and unmodified proteins made using a non-targeted cross-linking system.

The methods and compositions of the present invention can be used in conjunction with proteins and protein complexes from any suitable virus. In some embodiments the viruses are pathogenic viruses. In some embodiments the viruses are enveloped viruses, such as pathogenic enveloped viruses. In some embodiments the viruses are enveloped DNA and RNA viruses, such as, for example, Herpesviruses, including Alphaherpesvirinee, Betaherpesvirinae, Gammaherpesvirinae, Simplexvirus, Human herpesvirus 1, Varicellovirus, Human herpesvirus 3 (or Varicella-zoster virus), Mardivirus, Gallid herpesvirus 2, Iltovirus, Gallid herpesvirus 1, Cytomegalovirus, Human herpesvirus 5, Muromegalovirus, Murid herpesvirus 1, Roseolovirus, Human herpesvirus 6, Roseolovirus, Human herpesvirus 7, Proboscivirus, Elephantid herpesvirus 1, Lymphocryptovirus, Human herpesvirus 4 or Epstein-Barr virusm, Rhadinovirus, Human Herpesvirus 8, Saimiriine herpesvirus 2, Macavirus, Alcelaphine herpesvirus 1, Genus Percavirus, Equid herpesvirus 2, Cercopithecine, and Cercopithecine herpesvirus 1; Poxviruses, including the orthopox, parapox, yatapox, molluscipox, variola virus, vaccinia virus, cowpox virus, monkeypox virus, smallpox, orf virus, pseudocowpox, bovine papular stomatitis virus, tanapox virus, yaba monkey tumor virus, and molluscum contagiosum virus; Flaviviruses, including tick- and mosquito-borne, viruses with no known arthropod vector, Gadgets Gully virus (GGYV), Kadam virus (KADV), Kyasanur Forest disease virus (KFDV), Langat virus (LGTV), Omsk hemorrhagic fever virus (OHFV), Powassan virus (POWV), Royal Farm virus (RFV), Tick-borne encephalitis virus (TBEV), Louping ill virus (LIV), Meaban virus (MEAV), Saumarez Reef virus (SREV), Tyuleniy virus (TYUV), Aroa virus (AROAV), the Dengue virus group, Dengue virus (DENV), Kedougou virus (KEDV), the Japanese encephalitis virus group, Cacipacore virus (CPCV), Koutango virus (KOUV), Japanese encephalitis virus (JEV), Murray Valley encephalitis virus (MVEV), St. Louis encephalitis virus (SLEV), Usutu virus (USUV), West Nile virus (WNV), Yaounde virus (YAOV), Kokobera virus (KOKV), the Ntaya virus group, Bagaza virus (BAGV), Ilheus virus (ILHV), Israel turkey meningoencephalomyelitis virus (ITV), Ntaya virus (NTAV), Tembusu virus (TMUV), the Spondweni virus group, Zika virus (ZIKV), the Yellow fever virus group, Banzi virus (BANV), Bouboui virus (BOUV), Edge Hill virus (EHV), Jugra virus (JUGV), Saboya virus (SABV), Sepik virus (SEPV), Uganda S virus (UGSV), Wesselsbron virus (WESSV), Yellow fever virus (YFV), the Entebbe virus group, Entebbe bat virus (ENTV), Yokose virus (YOKV), the Modoc virus group, Apoi virus (APOIV), Cowbone Ridge virus (CRV), Jutiapa virus (JUTV), Modoc virus (MODV), Sal Vieja virus (SVV), San Perlita virus (SPV), the Rio Bravo virus group, Bukalasa bat virus (BBV), Carey Island virus (CIV), Dakar bat virus (DBV), Montana myotis leukoencephalitis virus (MMLV), Phnom Penh bat virus (PPBV), and the Rio Bravo virus (RBV); Togaviruses, including Alphavirus, Rubivirus, Sindbis virus, Eastern equine encephalitis virus, Western equine encephalitis virus, Venezuelan equine encephalitis virus, Ross River virus, O'nyong'nyong virus, and Rubella virus; Coronaviruses, including Group 1, Group 2, Group 3, Canine coronavirus (CCoV), Feline coronavirus (FeCoV), Human coronavirus 229E (HCoV-229E), Porcine epidemic diarrhea virus (PEDV), Transmissible gastroenteritis virus (TGEV), Human Coronavirus NL63 (NL or New Haven), Bovine coronavirus (BCoV), Canine respiratory coronavirus (CRCoV), Human coronavirus OC43 (HCoV-OC43), Mouse hepatitis virus (MHV), Porcine hemagglutinating encephalomyelitis virus (HEV), Rat coronavirus (RCV) Turkey coronavirus (TCoV), HCoV-HKU1, Infectious bronchitis virus (IBV), Turkey coronavirus (Bluecomb disease virus), and Severe acute respiratory syndrome coronavirus (SARS-CoV); Hepatitis D virus; Orthomyxoviruses, including influenza A, B, and C viruses, Infectious salmon anemia virus, and Thogotovirus; Mononegavirales; Paramyxoviruses, including the Paramyxovirinae, Pneumovirinae, Newcastle disease virus, Hendravirus, Nipahvirus, Measles virus, Rinderpest virus, Canine distemper virus, phocine distemper virus, Peste des Petits Ruminants virus (PPR), Sendai virus, Human parainfluenza viruses 1 and 3, some of the viruses of the common cold, Mumps virus, Simian parainfluenza virus 5, Menangle virus, Tioman virus, Tupaia paramyxovirus, Human respiratory syncytial virus, Bovine respiratory syncytial virus, Avian pneumovirus, Human metapneumovirus, Fer-de-Lance virus, Nariva virus, Tupaia paramyxovirus, Salem virus, J virus, Mossman virus, and Beilong virus; Rhabdoviruses, including the Vesicular stomatitis Indiana virus, Rabies virus, Bovine ephemeral fever virus, and Infectious haematopoetic necrosis virus; Bunyaviruses, including the Hantavirus; type species, Dugbe virus, Bunyamwera virus, Rift Valley fever virus, and Tenuivirus; Filoviruses, including five subtypes of the Ebola virus and the Marburg virus (Marburgvirus); Reoviruses, including Turreted and Nonturreted Reoviruses, Aquareovirus A, Cypovirus 1 (CPV 1), Fiji disease virus, Idnoreovirus 1, Mycoreovirus 1, Mammalian orthoreovirus, Colorado tick fever virus (CTFV), Bluetongue virus, Rotavirus A, and Seadornavirus; Hepadnaviruses, including Hepatitis B virus and Duck hepatitis B virus; and Retroviruses, including the Avian leukosis virus, Mouse mammary tumour virus, Murine leukemia virus, Feline leukemia virus, Bovine leukemia virus, Human T-lymphotropic virus, Walleye dermal sarcoma virus, Chimpanzee foamy virus, the Lentiviruses, the Simian and Feline immunodeficiency virus, the Human Immunodeficiency Virus Type 1, Group M and Subtypes A, B, C, D, E, F, G, H, I, J, and K, Group N, and Group O, and Human Immunodeficiency Virus Type 2; and any groups, subgroups, families, subfamilies, types, subtypes, genuses, species, strains, and/or clades of the any of the foregoing.

Diseases that may be caused by, or be associated with infection by, such pathogenic enveloped viruses include, but are not limited to, AIDS, Alzheimer's disease, atherosclerosis, bovine diarrhea, bovine ephemeral fever, bovine papular stomatitis, bronchiolitis, bronchitis, Burkitt's lymphoma, canine distemper, cold sores, chickenpox, chikungunya virus disease, cholangio carcinoma, chronic fatigue syndrome, the common cold, cowpox, Crohn's disease, diarrhea, dysautomnia, Dengue fever, encephalitis (in human and animal, e.g. equine), exanthem subitum, fibromyalgia, gastroenteritis, genital herpes, hantavirus pulmonary syndrome, hendra virus disease (haemorrhage and oedema of the lungs, and meningitis), hepatitis, hepatocarcinoma, Hodgkin's disease, infectious haematopoetic necrosis, infectious salmon anemia virus, influenza, Korean hemorrhagic fever, measles, mononucleosis, multiple sclerosis, mumps, Newcastle disease, nasopharyngeal carcinoma, pancreatic cancer, pancreatitis, *pityriasis rosea*, pneumonia, porcine transmissible gastroenteritis, rabies, respiratory tract infections (upper and lower respiratory tract), rinderpest, roseola *infantum*, shingles, small pox, vesicular stomatitis Indiana, viral hemorrhagic fevers, and west nile fever.

Nucleic acids encoding proteins/complexes of the present invention are provided. The proteins/complexes can be made by expressing nucleic acid sequences that encode them in vitro or in vivo by any known method known to one of ordinary skill in the art. Nucleic acids encoding proteins/complexes can be made by altering nucleic acid sequences encoding proteins/complexes by, for example, substitutions, additions (e.g., insertions) or deletions. The sequences can be cleaved at appropriate sites with restriction endonuclease (s), followed by further enzymatic modification if desired, isolated, and ligated in vivo or in vitro. Additionally, a nucleic acid sequence can be mutated in vitro or in vivo, to create and/or destroy translation, initiation, and/or termination sequences, or to create variations in coding regions and/or to form new, or destroy preexisting, restriction endonuclease sites to facilitate further in vitro modification.

Due to the degeneracy of nucleotide coding sequences, many different nucleic acid sequences can encode substantially the same residues in a protein/complex of the present invention. These can include nucleotide sequences comprising all, or portions of, a domain which is altered by the substitution of different codons that encode the same amino acid, or a functionally equivalent amino acid residue within the sequence, thus producing a "silent" (or functionally or phenotypically irrelevant) change, or a different amino acid residue with the sequence, thus producing a functionally or immunoglogically more beneficial change.

Any technique for mutagenesis known to one of ordinary skill in the art can be used, including but not limited to, enzymatic and chemical mutagenesis, in vitro site-directed mutagenesis, using, for example, the QuikChange Site-Directed Mutagenesis Kit (Stratagene), etc.

Any prokaryotic or eukaryotic cell can serve as the nucleic acid source for molecular cloning. A nucleic acid sequence encoding a protein or domain to be engineered for enhanced immunogenicity may be isolated from sources including prokaryotic, eukaryotic, mono-cellular, multi-cellular, animal, plant, fungus, vertebrate, mammalian, human, porcine, bovine, feline, equine, canine, avian, etc.

The nucleic acid may be obtained by any procedures known to one of ordinary skill in the art, for example, but not limited to, from cloned DNA (e.g., a DNA "library"), by chemical synthesis, by cDNA cloning, by the cloning of genomic DNA, or fragments thereof, e.g. purified from the desired cell (see e.g., Sambrook et al., 1985. Glover (ed.).

MRL Press, Ltd., Oxford, U.K.; vol. I, II). The nucleic acid may also be obtained by reverse transcribing cellular RNA, prepared by any of the methods known to one of ordinary skill in the art, such as random- or poly A-primed reverse transcription. Such nucleic acid may be amplified using any of the methods known to one of ordinary skill in the art, including PCR and 5' RACE techniques (Weis J. H. et al., 1992. Trends Genet. 8(8): 263-4; Frohman M A, 1994. PCR Methods Appl. 4(1): S40-58).

Whatever the source, the nucleic acid can be molecularly cloned into a suitable vector for propagation of the nucleic acid. Additionally, the nucleic acid may be cleaved at specific sites using various restriction enzymes, DNAse may be used in the presence of manganese, or the DNA can be physically sheared, as for example, by sonication. The linear DNA fragments can then be separated according to size by standard techniques, such as agarose and polyacrylamide gel electrophoresis and column chromatography.

Once nucleic acid fragments are generated, identification of specific nucleic acid fragments containing the desired sequences may be accomplished by any method known to one of ordinary skill in the art. As non-limiting examples, clones can be isolated by using PCR techniques that may either use two oligonucleotides specific for the desired sequence, or a single oligonucleotide specific for the desired sequence, using, for example, the 5' RACE system (Cale J M et al., 1998. Methods Mol. Biol. 105: 351-71; Frohman M A, 1994. PCR Methods Appl. 4(1): S40-58). The oligonucleotides may or may not contain degenerate nucleotide residues. Alternatively, if a portion of a nucleic acid is available and can be purified and labeled to generate a probe for nucleic acid hybridization (e.g. Benton and Davis, 1977. Science 196(4286): 180-2). Nucleic acid sequences with substantial homology to the probe will hybridize to it and can be detected and isolated. It may also be possible to identify the appropriate fragment by restriction enzyme digestion(s) and comparison of fragment sizes with those expected according to a known restriction map if such is available. Further selection can be carried out on the basis of the properties of the gene.

The presence of a desired nucleic acid may also be detected by assays based on the physical, chemical, or immunological properties of its expressed product. For example, cDNA clones, or DNA clones which hybrid-select the proper mRNAs, can be selected and expressed to produce a protein that has, for example, similar or identical electrophoretic migration, isoelectric focusing behavior, proteolytic digestion maps, hormonal or other biological activity, binding activity, or antigenic properties as known for a protein.

Using an antibody to a known protein, other proteins may be identified by binding of the labeled antibody to expressed putative proteins, for example, in an ELISA (enzyme-linked immunosorbent assay)-type procedure. Further, using a binding protein specific to a known protein, other proteins may be identified by binding to such a protein either in vitro or a suitable cell system, such as the yeast-two-hybrid system (see e.g. Clemmons D R, 1993. Mol. Reprod. Dev. 35: 368-74; Loddick S A, 1998 et al. Proc. Natl. Acad. Sci., U.S.A. 95:1894-98).

A gene can also be identified by mRNA selection using nucleic acid hybridization followed by in vitro translation. In this procedure, fragments are used to isolate complementary mRNAs by hybridization. Such DNA fragments may represent available, purified DNA of another species (e.g., Drosophila, mouse, human). Immunoprecipitation analysis or functional assays (e.g. aggregation ability in vitro, binding to receptor, etc.) of the in vitro translation products of the isolated products of the isolated mRNAs identifies the mRNA and, therefore, the complementary DNA fragments that contain the desired sequences.

In addition, specific mRNAs may be selected by adsorption of polysomes isolated from cells to immobilized antibodies specifically directed against protein. A radiolabeled cDNA can be synthesized using the selected mRNA (from the adsorbed polysomes) as a template. The radiolabeled mRNA or cDNA may then be used as a probe to identify the DNA fragments from among other genomic DNA fragments.

Alternatives to isolating the genomic nucleic acid sequences encoding a protein include chemically synthesizing the nucleic acid sequences or making cDNA from an mRNA which encodes the protein. For example, RNA for use in cDNA cloning of a nucleic acid encoding a protein of interest can be isolated from cells that express that protein.

The identified and isolated nucleic acid can be inserted into any appropriate cloning or expression vector known to one of ordinary skill in the art. A large number of vector-host systems known in the art may be used. Possible vectors include plasmids or modified viruses, but the vector system must be compatible with the host cell used. Such vectors include bacteriophages such as lambda derivatives, or plasmids such as PBR322 or pUC plasmid derivatives or the Bluescript vector (Stratagene).

The insertion into a cloning vector can, for example, be accomplished by ligating the DNA fragment into a cloning vector that has complementary cohesive termini. However, if the complementary restriction sites used to fragment the DNA are not present in the cloning vector, the ends of the DNA molecules may be enzymatically modified. Alternatively, any site desired may be produced by ligating nucleotide sequences (linkers) onto the DNA termini; these ligated linkers may comprise specific chemically synthesized oligonucleotides encoding restriction endonuclease recognition sequences. Furthermore, the gene and/or the vector may be amplified using PCR techniques and oligonucleotides specific for the termini of the gene and/or the vector that contain additional nucleotides that provide the desired complementary cohesive termini. In alternative methods, the cleaved vector and a gene may be modified by homopolymeric tailing (Cale J M et al., 1998. Methods Mol. Biol. 105: 351-71). Recombinant molecules can be introduced into host cells via transformation, transfection, infection, electroporation, etc., so that many copies of the gene sequence are generated.

In specific embodiments, transformation of host cells with recombinant DNA molecules that incorporate an isolated gene, cDNA, or synthesized DNA sequence enables generation of multiple copies of the gene. Thus, the gene may be obtained in large quantities by growing transformants, isolating the recombinant DNA molecules from the transformants and, when necessary, retrieving the inserted gene from the isolated recombinant DNA.

The sequences provided by the present invention include those nucleotide sequences encoding substantially the same amino acid sequences as found in native proteins, and those encoded amino acid sequences with functionally equivalent amino acids, as well as those encoding other derivatives or analogs, as described below for derivatives and analogs.

The amino acid sequence of a protein may be derived by any method known to one of ordinary skill in the art. For example, the sequence can be derived by deduction from the DNA sequence, or alternatively, by direct sequencing of the protein, for example, with an automated amino acid sequencer.

A protein sequence may be further characterized by any method known to one of ordinary skill in the art. For example, a protein can be characterized by a hydrophilicity analysis (Hopp T P & Woods K R, 1981. Proc. Natl. Acad. Sci., U.S.A. 78: 3824). A hydrophilicity profile can be used to identify the hydrophobic and hydrophilic regions of the protein and the corresponding regions of the gene sequence, which encode such regions.

Secondary, structural analysis may be carried out by any method known to one of ordinary skill in the art (e.g. Chou P Y & Fasman G D, 1974. Biochemistry 13(2): 222-45). For example, secondary structural analysis can also be done, to identify regions of a protein that assume specific secondary structures. Manipulation, translation, and secondary structure prediction, open reading frame prediction and plotting, as well as determination of sequence homologies, can also be accomplished using computer software programs available in the art. Other methods of structural analysis include X-ray crystallography, nuclear magnetic resonance spectroscopy and computer modeling.

The nucleotide sequence coding for a protein/complex can be inserted into an appropriate expansion or expression vectors, i.e., a vector which contains the necessary elements for the transcription alone, or transcription and translation, of the inserted protein-coding sequence(s). The native genes and/or their flanking sequences can also supply the necessary transcriptional and/or translational signals.

Expression of a nucleic acid sequence encoding a protein or protein complex may be regulated by a second nucleic acid sequence so that the polypeptide is expressed in a host transformed with the recombinant DNA molecule. For example, expression of a polypeptide may be controlled by any promoter/enhancer element known in the art.

Promoters which may be used to control gene expression include, as examples, the SV40 early promoter region, the promoter contained in the 3' long terminal repeat of Rous sarcoma, the herpes thymidine kinase promoter, the regulatory sequences of the metallothionein gene; prokaryotic expression vectors such as the β-lactamase promoter, or the lac promoter; plant expression vectors comprising the nopaline synthetase promoter or the cauliflower mosaic virus 35S RNA promoter, and the promoter of the photosynthetic enzyme ribulose biphosphate carboxylase; promoter elements from yeast or other fungi such as the Gal 4 promoter, the alcohol dehydrogenase promoter, phosphoglycerol kinase promoter, alkaline phosphatase promoter, and the following animal transcriptional control regions, which exhibit tissue specificity and have been utilized in transgenic animals: elastase I gene control region which is active in pancreatic acinar cells (Swift et al. Cell; vol. 38: pp. 639-646, 1984); a gene control region which is active in pancreatic beta cells (Hanahan D., Nature; vol. 315: pp. 115-122, 1985), an immunoglobulin gene control region which is active in lymphoid cells (Grosschedl R. et al. Cell; vol. 38: pp. 647-658, 1984), mouse mammary tumor virus control region which is active in testicular, breast, lymphoid and mast cells (Leder A. et al. Cell; vol. 45: pp. 45-495, 1986), albumin gene control region which is active in liver (Pinkert C. A. et al. Genes Dev.; vol. 1: pp. 268-276, 1987), alpha-fetoprotein gene control region which is active in liver (Krumlauf R. et al. Mol. Cell. Biol.; vol. 5: pp. 1639-1648, 1985); alpha 1-antitrypsin gene control region which is active in the liver (Kelsey G. D. et al. Genes Dev.; vol. 1: pp. 161-171, 1987), beta-globin gene control region which is active in myeloid cells (Magram J. et al. Nature; vol. 315: pp. 338-340, 1985); myelin basic protein gene control region which is active in oligodendrocyte cells in the brain (Readhead C. et al. Cell; vol. 48: pp. 703-712, 1987); myosin light chain-2 gene control region which is active in skeletal muscle (Shani M. Nature; vol. 314: pp. 283-286, 1985), and gonadotropic releasing hormone gene control region which is active in the hypothalamus (Mason A. J. et al. Science; vol. 234: pp. 1372-1378, 1986).

In some embodiments a vector is used that comprises a promoter operably linked to a nucleic acid, one or more origins of replication, and, optionally, one or more selectable markers (e.g., an antibiotic resistance gene). In bacteria, the expression system may comprise the lac-response system for selection of bacteria that contain the vector. Expression constructs can be made, for example, by subcloning a coding sequence into one the restriction sites of each or any of the pGEX vectors (Pharmacia, Smith D. B. and Johnson K. S. Gene; vol. 67: pp. 31-40, 1988). This allows for the expression of the protein product.

Vectors containing nucleic acid inserts can be identified by several different approaches, including: (a) identification of specific one or several attributes of the nucleic acid itself, such as, for example, fragment lengths yielded by restriction endonuclease treatment, direct sequencing, PCR, or nucleic acid hybridization; (b) presence or absence of "marker" functions; and, where the vector is an expression vector, (c) expression of inserted sequences. In the first approach, the presence of a gene inserted in a vector can be detected, for example, by sequencing, PCR or nucleic acid hybridization using probes comprising sequences that are homologous to an inserted gene. In the second approach, the recombinant vector/host system can be identified and selected based upon the presence or absence of certain "marker" gene functions (e.g., thymidine kinase activity, resistance to antibiotics, transformation phenotype, occlusion body formation in baculovirus, etc.) caused by the insertion of a gene in the vector. For example, if the nucleic acid is inserted within the marker gene sequence of the vector, recombinants containing the insert an identified by the absence of the marker gene function. In the third approach, recombinant expression vectors can be identified by assaying the product expressed by the recombinant expression vectors containing the inserted sequences. Such assays can be based, for example, on the physical or functional properties of the protein in in vitro assay systems, for example, binding with anti-protein antibody.

Once a particular recombinant nucleic acid molecule is identified and isolated, several methods known in the art may be used to propagate it. Once a suitable host system and growth conditions are established, recombinant expression vectors can be propagated and prepared in quantity. Some of the expression vectors that can be used include human or animal viruses such as vaccinia virus or adenovirus; insect viruses such as baculovirus; yeast vectors; bacteriophage vectors (e.g., lambda phage), and plasmid and cosmid DNA vectors.

Once a recombinant vector that directs the expression of a desired sequence is identified, the gene product can be analyzed. This is achieved by assays based on the physical or functional properties of the product, including radioactive labeling of the product followed by analysis by gel electrophoresis, immunoassay, etc.

A variety of host-vector systems may be utilized to express the protein-coding sequences. These include, as examples, mammalian cell systems infected with virus (e.g., vaccinia virus, adenovirus, etc.); insect cell systems infected with virus (e.g., baculovirus); microorganisms such as yeast containing yeast vectors, or bacteria transformed with bacteriophage, DNA, plasmid DNA, or cosmid DNA. The expression elements of vectors vary in their strengths and specificities. Depending on the host-vector system utilized, any one of a number of suitable transcription and translation elements may be used.

In some embodiments the gene may be expressed in bacteria that are protease deficient, and that have low constitutive levels and high induced levels of expression where an expression vector is used that is inducible, for example, by the addition of IPTG to the medium.

In yet another embodiment, the proteins/complexes may be expressed with signal peptides, such as, for example, pelB bacterial signal peptide, that directs the protein to the bacterial periplasm (Lei et al. J. Bacteril., vol. 169: pp. 4379, 1987). Alternatively, protein may be allowed to form inclusion bodies, and subsequently be resolubilzed and refolded (Kim S. H. et al. Mo Immunol, vol. 34: pp. 891, 1997).

In yet another embodiment, a fragment of one, any, both, several or all of the proteins a complex comprising one or more domains of the protein is expressed. Any of the methods previously described for the insertion of DNA fragments into a vector may be used to construct expression vectors containing a chimeric gene consisting of appropriate transcriptional/translational control signals and the protein coding sequences. These methods may include in vitro recombinant DNA and synthetic techniques and in vivo recombinants (genetic recombination).

In addition, a host cell strain may be chosen that modulates the expression of the inserted sequences, or modifies and processes the gene product in the specific fashion desired. Expression from certain promoters can be elevated in the presence of certain inducers; thus, expression of the genetically engineered polypeptides may be controlled. Furthermore, different host cells have characteristic and specific mechanisms for the translational and post-translational processing and modification (e.g., glycosylation, phosphorylation of proteins. Appropriate cell lines or host systems can be chosen to ensure the desired modification and processing of the foreign polypeptide(s) expressed. For example, expression in a bacterial system can be used to produce a non-glycosylated core protein product. Expression in yeast will produce a glycosylated product. Expression in mammalian cells can be used to ensure "native" glycosylation of a heterologous protein. Furthermore, different vector/host expression systems may effect processing reactions to different extents.

In other embodiments of the invention, proteins and complexes of the present invention, and any derivates, analogs, orthologs, homologs, or fragments thereof, and one, any, both, several or all of the polypeptides a complex, and any derivates, analogs, orthologs, homologs, or fragments thereof may be expressed as a fusion-, or chimeric, protein product (comprising the protein, fragment, analog, or derivative joined via a peptide bond to a heterologous protein sequence of a different protein). Such a chimeric product can be made by ligating the appropriate nucleic acid sequences encoding the desired amino acid sequences to each other by methods known in the art, in the proper coding frame, and expressing the chimeric product by methods commonly known in the art. Alternatively, such a chimeric product may be made by protein synthetic techniques, for example, by use of a peptide synthesizer.

The proteins and protein complexes may be expressed together in the same cells either on the same vector, driven by the same or independent transcriptional and/or translational signals, or on separate expression vectors, for example by cotransfection or cotransformation and selection, for example, may be based on both vectors' individual selection markers. Alternatively, proteins/complexes may be expressed separately; they may be expressed in the same expression system, or in different expression systems, and may be expressed individually or collectively as fragments, derivatives or analogs of the original polypeptide.

Any method known to one of ordinary skill in the art may be used to identify epitopes of polypeptides and one, any, both, several or all of the polypeptides a complex, and any derivates, analogs, orthologs, homologs, fragments, chimers, or fusion proteins thereof, that are immunogenic, and that lead to the production of neutralizing and/or broadly neutralizing antibodies. Such methods may, as non-limiting examples, be computational or based on antigenic studies using antibodies known to be neutralizing and/or broadly neutralizing or using neutralizing and/or broadly neutralizing antibodies that result from immunization with polypeptides and one, any, both, several or all of the polypeptides a complex, and any derivates, analogs, orthologs, homologs, fragments, chimers, or fusion proteins thereof.

Antigenic analyses, i.e. the determination of whether the engineered polypeptides and one, any, both, several or all of the polypeptides a complex, and any derivates, analogs, orthologs, homologs, fragments, chimers, or fusion proteins thereof, bind specific antibodies known to bind to any, or to specific antigenic structures of a particular conformation of a polypeptide or protein of the present invention, or any derivate, analog, ortholog, homolog, fragment, chimer, or fusion protein thereof, and one, any, both, several or all of the polypeptides a complex, and any derivates, analogs, orthologs, homologs, fragments, chimers, or fusion proteins thereof, may be performed by any method known in the art. Such methods include, as non-limiting examples, those described in detail by Dey et al. 2007 (Dey et al., 2007. Characterization of Human Immunodeficiency Virus Type 1 Monomeric and Trimeric gp120 Glycoproteins Stabilized in the CD4-Bound State: Antigenicity, Biophysics, and Immunogenicity. J Virol 81(11): 5579-5593), Binley et al., 2000 (Binley et al., 2000. A Recombinant Human Immunodeficiency Virus Type 1 Envelope Glycoprotein Complex Stabilized by an Intermolecular Disulfide Bond between the gp120 and gp41 Subunits Is an Antigenic Mimic of the Trimeric Virion-Associated Structure. J Virol 74(2): 627-643), Pancera et al., 2005 (Pancera et al., 2005. Soluble Mimetics of Human Immunodeficiency Virus Type 1 Viral Spikes Produced by Replacement of the Native Trimerization Domain with a Heterologous Trimerization Motif: Characterization and Ligand Binding Analysis. J Virol 79(15): 9954-9969), and Beddows et al., 2006 (Beddows et al., 2006. Construction and Characterization of Suluble, Cleaved, and Stabilized Trimeric Env proteins Based on HIV Type 1 env Subtype A. AIDS Res Hum Retroviruses 22(6): 569-579).

Immunogenic analyses, i.e. the determination of whether the engineered polypeptides and one, any, both, several or all of the polypeptides a complex, and any derivates, analogs, orthologs, homologs, fragments, chimers, or fusion proteins thereof, used as immunogens generate antibodies known to bind to specific antigenic structures of any, or of any particular conformation of a polypeptide or protein of the present invention, or any derivate, analog, ortholog, homolog, fragment, chimer, or fusion protein thereof, and one, any, both, several or all of the polypeptides a complex, and any derivates, analogs, orthologs, homologs, fragments, chimers, or fusion proteins thereof, may be performed by any method known in the art. Such methods include, as non-limiting examples, those described in detail by Dey et al. 2007 (Dey et al., 2007. Characterization of Human Immunodeficiency Virus Type 1 Monomeric and Trimeric gp120 Glycoproteins Stabilized in the CD4-Bound State: Antigenicity, Biophysics, and Immunogenicity. J Virol 81(11): 5579-5593) and Beddows et al., 2006 (Beddows et al., 2007. A comparative immunogenicity study in rabbits of disulfide-stabilized proteolytically cleaved, soluble trimeric human immunodeficiency virus type 1 gp140, trimeric cleavage-defective gp140 and momomeric gp120. Virol 360: 329-340).

Neutralization assays, i.e. the determination of whether antibodies or antisera generated by immunization of vertebrates, preferably mammals, such as, for example, but not limited to mice, rabbits, or primates, with the engineered polypeptides and one, any, both, several or all of the polypeptides a complex, and any derivates, analogs, orthologs, homologs, fragments, chimers, or fusion proteins thereof, have viral neutralizing activity, may be performed by any method known in the art. Such methods include, as non-limiting examples, those described in detail by Dey et al. 2007 (Dey et al., 2007. Characterization of Human Immunodeficiency Virus Type 1 Monomeric and Trimeric gp120 Glycoproteins Stabilized in the CD4-Bound State: Antigenicity, Biophysics, and Immunogenicity. J Virol 81(11): 5579-5593) and Beddows et al., 2006 (Beddows et al., 2007. A comparative immunogenicity study in rabbits of disulfide-stabilized proteolytically cleaved, soluble trimeric human immunodeficiency virus type 1 gp140, trimeric cleavage-defective gp140 and momomeric gp120. Virol 360: 329-340).

Biophysical analyses, i.e. the determination of any biophysical characteristics known in the art, such as, for example, but not limited to, stability of engineered polypeptides and of one, any, both, several or all of the polypeptides a complex, and any derivates, analogs, orthologs, homologs, fragments, chimers, or fusion proteins thereof, and of the complex itself, may be performed by any method known in the art.

Stability of the engineered material may be tested in vitro in, as examples, but not limited to, denaturing and non-denaturing electrophoresis by any methods known to one of ordinary skill in the art, by isothermal titration calorimetry, as described in detail in Dey et al., 2007 ((Dey et al., 2007. Characterization of Human Immunodeficiency Virus Type 1 Monomeric and Trimeric gp120 Glycoproteins Stabilized in the CD4-Bound State: Antigenicity, Biophysics, and Immunogenicity. J Virol 81(11): 5579-5593), and time-course experiments incubating the polypeptides and one, any, both, several or all of the polypeptides a complex, and any derivates, analogs, orthologs, homologs, fragments, chimers, or fusion proteins thereof, at varying protein concentrations and temperatures; the engineered material's stability may also be tested at various pH levels and in various redox conditions. For the above conditions, as non-limiting examples, the antigenicity, immunogenicity, and neutralization capacity of the polypeptides and one, any, both, several or all of the polypeptides a complex, and any derivates, analogs, orthologs, homologs, fragments, chimers, or fusion proteins thereof, are determined by assaying as described above. Proteins may be incubated at varying temperatures in serum, or other biologically derived media, and may be analyzed for susceptibility to proteolytic degradation by any methods known to one of ordinary skill in the art.

To determine the utility of an engineered polypeptide, protein, or protein complex more directly, biodistribution and/or other pharmacokinetic attributes may be determined. In a specific embodiment engineered material may be injected into a model organism and assayed for by tracing a marker, such as, for example, but not limited to, $^{125}$I or $^{18}$F radio labels (Choi C W et al, 1995. Cancer Research 55: 5323-29), and/or by tracing activity as described above (Colcher D et al., 1998. Q. J. Nucl. Med. 44(4): 225-41). Relevant information may be obtained, for example, by determining the amount of material that can be expected to be immunogenically active due to its penetration of the targeted tissue. Half-life in circulation and at the targeted tissue, clearance, immunogenicity, and speed of penetration may also be determined in this context.

The most conclusive measurements with regard to a conjugate's utility as a vaccine immunogen are to determine its immunogenic activity directly clinically. In a specific embodiment, such studies may assess, for example, but not limited to, the level of protection afforded by engineered polypeptides and one, any, both, several or all of the polypeptides a complex, and any derivates, analogs, orthologs, homologs, fragments, chimers, or fusion proteins thereof. For example, a comparison may be made between placebo and immunogen vaccinated groups with regard to their rates of infection (or sero-conversion). As another non-limiting example, the therapeutic capacity of the engineered polypeptides and one, any, both, several or all of the polypeptides a complex, and any derivates, analogs, orthologs, homologs, fragments, chimers, or fusion proteins thereof, may be assesses. For example, a comparison may be made between placebo and immunogen vaccinated groups with regard to their viral loads, or, in the case of an HIV vaccine, as a non-limiting example, with regard CD4 cell counts.

This invention provides software that permits automated selection of suitable residues at which a polypeptide, protein, or protein complex may be modified for crosslinking. Such software can be used in accordance with the selection process, as described above, and with geometrical, physical, and chemical criteria, such as set forth in the US Patent "Stabilized Proteins" (Marshall C P et al., U.S. Pat. No. 7,445,912; see especially Identification of Suitable Residue Pairs for the Reaction, Software for the Residue Selection Process in Section 5, and the Residue Pair Selection Flowchart in Section 6).

In some embodiments the present invention is directed to pharmaceutical compositions, and administration of such pharmaceutical compositions to subjects. In some embodiments the subjects are animal species. In some the subjects are mammalian animal species. In some embodiments the subject are humans. In some embodiments the pharmaceutical compositions of the invention may comprise, or consist essentially of, the engineered proteins and protein complexes described herein. In some embodiments the engineered proteins or protein complexes of the present invention may be provided in pharmaceutical composition that comprises one or more additional active components, such as one or more additional vaccine immunogens. In some embodiments the engineered proteins and/or protein complexes of the invention may be provided in a pharmaceutical composition that comprises one or more other components, including, but not limited to, pharmaceutically acceptable carriers, adjuvants, wetting or emulsifying agents, pH buffering agents, preservatives, and/or any other components suitable for the intended use of the pharmaceutical compositions. These pharmaceutical compositions of the invention can take the form of solutions, suspensions, emulsions and the like. The term "pharmaceutically acceptable carrier"

includes various diluents, excipients and/or vehicles in which, or with which, the engineered proteins and protein complexes of the invention can be provided. The term "pharmaceutically acceptable carrier" includes, but is not limited to, carriers known to be safe for delivery to human and/or other animal subjects, and/or approved by a regulatory agency of the Federal or a state government, and/or listed in the U.S. Pharmacopeia, and/or other generally recognized pharmacopeia, and/or receiving specific or individual approval from one or more generally recognized regulatory agencies for use in humans and/or other animals. Such pharmaceutically acceptable carriers, include, but are not limited to, water, aqueous solutions (such as saline solutions, buffers, and the like), organic solvents (such as certain alcohols and oils, including those of petroleum, animal, vegetable or synthetic origin, such as peanut oil, soybean oil, mineral oil, sesame oil), and the like. Adjuvants that may be used include, but are not limited to, inorganic or organic adjuvants, oil-based adjuvants, virosomes, liposomes, lipopolysaccharide (LPS), molecular cages for antigens (such as immune-stimulating complexes ("ISCOMS")), Ag-modified saponin/cholesterol micelles that form stable cage-like structures that are transported to the draining lymph nodes), components of bacterial cell walls, endocytosed nucleic acids (such as double-stranded RNA (dsRNA), single-stranded DNA (ssDNA), and unmethylated CpG dinucleotide-containing DNA), AUM, aluminum phosphate, aluminum hydroxide, and Squalene. In one embodiments virosomes are used as an adjuvant. Virosomes are known to have an excellent safety profile, and may contain membrane-bound proteins such as hemagglutinin and neuraminidase derived from the influenza virus, which mediate fusogenic activity and can thereby facilitate uptake of an immunogen (such as the engineered proteins and protein complexes of the invention) by antigen presenting cells and induce the antigen-processing pathway. Additional commercially available adjuvants that can be used in accordance with the present invention include, but are not limited to, the Ribi Adjuvant System (RAS, an oil-in-water emulsion containing detoxified endotoxin (MPL) and mycobacterial cell wall components in 2% squalene (Sigma M6536)), TiterMax (a stable, metabolizable water-in-oil adjuvant (CytRx Corporation 150 Technology Parkway Technology Park/Atlanta Norcross, Ga. 30092)), Syntex Adjuvant Formulation (SAF, an oil-in-water emulsion stabilized by Tween 80 and pluronic polyoxyethlene/polyoxypropylene block copolymer L121 (Chiron Corporation, Emeryville, Calif.)), Freund's Complete Adjuvant, Freund's Incomplete Adjuvant, ALUM—aluminum hydroxide, Al(OH)3 (available as Alhydrogel, Accurate Chemical & Scientific Co, Westbury, N.Y.), SuperCarrier (Syntex Research 3401 Hillview Ave. P.O. Box 10850 Palo Alto, Calif. 94303), Elvax 40W1,2 (an ethylene-vinyl acetate copolymer (DuPont Chemical Co. Wilmington, Del.)), L-tyrosine co-precipitated with the antigen (available from numerous chemical companies); Montanide (a manideoleate, ISA Seppic Fairfield, N.J.)), AdjuPrime (a carbohydrate polymer), Nitrocellulose-absorbed protein, Gerbu adjuvant (C-C Biotech, Poway, Calif.), and the like.

In some embodiments the pharmaceutical compositions of the invention comprise an "effective amount" of a protein or protein complex of the invention. An "effective amount" is an amount required to achieve a desired end result. Examples of desired end results include, but are not limited to, the generation of a humoral immune response, the generation of a neutralizing antibody response, the generation of a broadly neutralizing antibody response, and the generation of protective immunity. The amount of an engineered protein or protein complex of the invention that is effective to achieve the desired end result will depend on variety of factors including, but not limited to, the nature of the virus against which protection or some other therapeutic effect is sought, the nature of the protein or protein complex, the species of the intended subject (e.g. whether a human or some other animal species), the age and/or sex of the intended subject, the planned route of administration, the planned dosing regimen, the seriousness of the disease or disorder, and the like. The effective amount—which may be a range of effective amounts—can be determined by standard techniques without any undue experimentation, for example using in vitro assays and/or in vivo assays in the intended subject species or any suitable animal model species. Suitable assays include, but are not limited to, those that involve extrapolation from dose-response curves and/or other data derived from in vitro and/or in vivo model systems. In some embodiments the effective amount may be determined according to the judgment of a medical or veterinary practitioner based on the specific circumstances.

Various delivery systems are known in the art and any suitable delivery systems can be used to administer the pharmaceutical compositions of the present invention. Such systems include, but are not limited to, intradermal, intramuscular, intraperitoneal, intravenous, subcutaneous, intranasal, epidural, and oral delivery systems. The pharmaceutical compositions may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it may be desirable to introduce the pharmaceutical compositions of the invention into the central nervous system by any suitable route, including intraventricular and intrathecal injection. Intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent.

In some embodiments it may be desirable to administer the pharmaceutical compositions of the invention locally to a tissue in which the engineered protein or protein complex may be most effective in generating a desirable outcome. This may be achieved by, for example, local infusion, injection, delivery using a catheter, or by means of an implant, such as a porous, non-porous, or gelatinous implant or an implant comprising one or more membranes (such as sialastic membranes) or fibers from or through which the protein or protein complexes may be released locally. In some embodiments a controlled release system may be used. In some embodiments a pump may be used (see Langer, supra; Sefton, 1987. CRC Crit. Ref. Biomed. Eng. 14: 201; Buchwald et al., 1980. Surgery 88: 507; Saudek et al., 1989. N. Engl. J. Med. 321: 574). In some embodiments polymeric materials may be used to facilitate and/or control release of the protein or protein complexes of the invention (see Medical Applications of Controlled Release, Langer and Wise (eds.), 1974. CRC Pres., Boca Raton, Fla.; Controlled Drug Bioavailability, 1984. Drug Product Design and Performance, Smolen and Ball (eds.), Wiley, New York; Ranger & Peppas, 1983 Macromol. Sci. Rev. Macromol. Chem. 23: 61; see also Levy et al., 1985. Science 228:190; During et al, 1989. Ann. Neurol. 25: 351; Howard et al., 1989. J. Neurosurg 71:105). In some embodiments a controlled release system can be placed in proximity to the tissue/organ to which the protein or protein complex is to be delivered (see, e.g., Goodson, 1984. in Medical Applications of Controlled Release, supra, vol. 2: 115-138). Some suitable controlled release systems that may be used in conjunction with the present invention are described Langer, 1990, Science; vol. 249: pp. 527-1533.

EXAMPLES

There has been much focus in HIV vaccine development on engineering soluble versions of stabilized HIV envelope (Env) glycoproteins that recapitulate properties of the functional Env trimer for use as immunogens. This approach is taken because gp120 on its own does not efficiently elicit immune responses that generate broadly neutralizing antibodies. Broadly neutralizing antibodies to gp120 have, however, been isolated from patients.

HIV has evolved several mechanisms of immune evasion inherent in the unmodified HIV envelope glycoproteins. These strategies are based, in part, on HIV's high rate of mutation, the spike's lability, and the presence of immunodominant variable loops that divert antibody responses from functionally conserved epitopes and allow the escape of viruses with non-cross reactive variable loops. More importantly, however, gp120-receptor interactions involve significant conformational reorganization, and recognition by antibodies that bind the conserved CD4 receptor binding site (CD4BS) induces conformational change; current theory is that the resulting "conformational mask" allows conserved protein surfaces, such as the CD4BS, to assume various conformations not displayed on the functional spike, and enables HIV-1 to maintain functionality (receptor binding) while resisting neutralization (Kwong et al. 2002. HIV-1 evades antibody-mediated neutralization through conformational masking of receptor-binding sites. Nature 420:678-82; Phogat et al, 2007. Rational modifications of HIV-1 envelope glycoproteins for immunogen design. Curr Pharm Design 13: 213-227). Some previous studies have suggested that stabilization of envelope proteins in particular conformations can counteract the conformational masking strategy of viruses to evade host immune systems, and stabilize epitopes that are otherwise poorly or not at all recognized and bound by neutralizing and broadly neutralizing antibodies, and therefore are not secreted by plasma B cells in response to infection. See, for example, Dey et al., 2007. Characterization of Human Immunodeficiency Virus Type 1 Monomeric and Trimeric gp120 Glycoproteins Stabilized in the CD4-Bound State: Antigenicity, Biophysics, and Immunogenicity. J Virol 81(11): 5579-5593). Stabilization of the soluble ecto-gp41-gp120 complex (gp140) by introducing a disulfide bond provides a construct that binds neutralizing antibodies, but that nonetheless elicits protective humoral immune responses in animals that are limited in breadth (Beddows et al., 2007. A Comparative Immunogenicity Study in Rabbits of Disulfide-stabilized, Proteolytically Cleaved, Soluble Trimeric Human Immunodeficiency Virus Type I gp140, Trimeric Cleavage-Defective gp140 and Monomeric gp120. Virology 360: 329-340). Mutations reported to stabilize gp120 in a functionally active conformation allow binding of the broadly neutralzing MAb b12 (which binds the conserved CD4BS), and antisera to gp120 stabilized by these mutations demonstrates an improvement in their capacity to neutralize a panel of clade B viruses (Dey et al., 2007. Characterization of Human Immunodeficiency Virus Type 1 Monomeric and Trimeric gp120 Glycoproteins Stabilized in the CD4-Bound State: Antigenicity, Biophysics, and Immunogenicity. J Virol 81(11): 5579-5593). More recently, the cryo-electron tomographic structure of the trimeric HIV spike has been elucidated at 20 Å resolution, providing structural information of the spike in unliganded and CD4- and Ab-complexed conformations (Liu et al., 2008. Molecular architecture of native HIV-1 gp120 trimers. Nature 455: 109). These studies demonstrates that trimerization is mediated by gp41 and that the three V1/V2 loops of gp120 come together to form the apex of the spike in the unliganded and b12 and CD4 complexed conformations. Together, these studies suggest that stabilizing the HIV spike in a particular conformation (which binds neutralizing antibodies) may be a way to counteract conformational masking and obtain an immunogen that elicits broadly protective Ab responses.

Previous studies attempted to stabilize the soluble ecto-gp41-gp120 complex (gp140) of the HIV virus by introducing disulfide bonds, and generated a construct that bound to neutralizing antibodies. See Beddows et al., 2007, "A Comparative Immunogenicity Study in Rabbits of Disulfide-stabilized, Proteolytically Cleaved, Soluble Trimeric Human Immunodeficiency Virus Type I gp140, Trimeric Cleavage-Defective gp140 and Monomeric gp120," Virology, Vol. 360: pp 329-340. However, disulfide bonds are known to be pH sensitive and to be dissolved under certain redox conditions such that the preventative and/or therapeutic utility of polypeptides, proteins, or protein complexes engineered with disulfide crosslinks used as immunogens in vivo may be compromised. Furthermore, undesired disulfide bonds often form between proteins with free sulfhydryl groups that mediate aggregate formation. As such there is a need for alternative methods of crosslinking HIV gp120 and ecto-gp41 proteins.

Example 1

Stabilization of the protein-protein interactions of the HIV trimeric spike via the V1/V2 loop stabilizes the folds of the protein conformations such that the complex has the capacity to elicit neutralizing or broadly neutralizing humoral immune responses. Liu et al. described the three-dimensional structure of the HIV-1 spike in complex with a broadly neutralizing antibody (Liu et al., 2008, Molecular architecture of native HIV-1 gp120 trimers. Nature 455: 109). Based on an analysis of this structure, residues of the V1/V2 loop distal to the stem between positions 143 and 150, and between positions 160 and 180 were selected for formation of dityrosine bonds.

The selected residues are mutated in pair-wise combinations to tyrosine (where tyrosine is not already present), subjected to crosslinking conditions, whereby the HIV spike is bound and unbound to soluble CD4 and the b12 neutralizing antibody, and analyzed for dityrosine bond formation leading to trimerization. Covalent trimerization requires a minimum of two dityrosine bonds to form.

The pcDNA3.1 (Stratagene) vector that is suitable for amplification, mutagenesis, and both stable and transient expression of the HIV proteins and protein complexes. Targeted point mutations in the HIV Env gene are introduced in a pair-wise manner (e.g. 1 in gp120 and 1 in gp41) using the QuikChange Site-Directed Mutagenesis Kit (Stratagene) according to the manufacturer's instructions to generate mutated/engineered proteins. The mutated/engineered proteins are expressed in serum-free medium by transient transfection of HEK293T cells. HEK293T cells growing in Dulbecco's modified Eagle's medium with 10% fetal bovine serum, 2 mM glutamine, and 1× penicillin-streptomycin (50 units/ml penicillin, 50 □g/ml streptomycin) are seeded at a density of 1.2×10⁷ cells per 150 cm² tissue culture dish, and grown overnight. After the overnight incubation, cells are transfected with a mixture of the expression vector and the transfection reagent Fugene (Roche) according to the manufacturer's instructions. After approximately 24 hours, the transfection medium is replaced with 293 SFMII (serum-free medium) supplemented with 4 mM glutamine. After another four days, supernatants are collected, and centrifuged at 3,500×g. Supernatants are filtered through sterile 0.2-□m filters and protease inhibitors are added. Prior to protein purification, supernatants can be stored at 4° C. for no more than 1 week.

Protein purification is performed using affinity purification columns, and the trimeric fractions are isolated by size exclusion chromatography. An anti-gp120 antibody-coupled affinity column is used for the affinity purification. The culture supernatant is applied to the affinity column overnight at room temperature, and the column is washed with 10 volumes of phosphate-buffered saline (PBS) (pH 7.4) containing 0.5 M NaCl and washed with 5 volumes of PBS containing 0.15M NaCl, and eluted with 100 mM glycine (pH 2.8). The trimeric proteins are eluted with 3 M MgCl2 prepared in 20 mM Tris-HCl (pH 7.4), and protein concentrations are monitored by optical density (OD) at 280 nm. Eluted fractions containing protein are pooled, concentrated with Amicon Ultra centrifugal filter devices (Millipore, Bedford, Mass.), and dialyzed extensively against PBS (pH 7.4) containing protease inhibitors. Affinity-purified trimeric protein is further subjected to size exclusion chromatography using a Superdex 200 16/26 column (Amersham Pharmacia) in PBS containing 0.35 M NaCl and protease inhibitors. The flow rate is set to 1 ml/min for the first 100 min and reduced to 0.5 ml/min until the end of the run, which allowed the separation of the oligomeric species. Trimeric protein containing fractions are pooled, concentrated as described above, dialyzed against PBS (pH 7.4) containing protease inhibitors, flash-frozen, and stored at −80° C.

For dityrosine crosslinking protein aliquots are subjected to reaction conditions that lead to the formation of dityrosine (DT) bonds in control proteins. The reaction is catalyzed enzymatically using the Arthromyces Peroxidase as described in detail in Malencik & Anderson, 1996, Biochemistry 35: 4375-86. DT bond formation is monitored and quantified by spectrophotometry with an excitation wavelength of 320 nm, and fluorescence measured at a wavelength of 400 nm using a dityrosine standard (and a standard curve), as described in detail in Malencik & Anderson, 2003, Amino Acids 25: 233-247, while loss of tyrosyl fluorescence is monitored also monitored by standard procedures. When loss of tyrosyl florescence is no longer stoicometric with DT bond formation, the reaction is stopped by the addition of a reducing agent and subsequent cooling (on ice) or freezing of the sample.

Constructs that are revealed to form dityrosine crosslinks are further purified by standard chromatographic methods, including, for example, size chromatography described above, under mildly denaturing conditions that do not cause denaturation, but rather only dissociation of uncrosslinked monomers. Purified crosslinked constructs are further analyzed, as described below.

Biophysical Analysis
Gel Electrophoresis

Standard methods for denaturing and non-denaturing proteins are applied to confirm, for example, the degree of crosslinking, and to confirm that the crosslinking is specifically directed to the targeted tyrosyl side chains (and that the constructs do not form mulitmers, concatamers, etc.).

Isothermal Titration Calorimetry (Itc)

The degree of thermodynamic stabilization of the dityrosine crosslinked dimeric complex is quantified by standard ITC methods using sCD4 as a ligand and a VP-ITC titration calorimeter system from MicroCal, Inc. Protein samples are dialyzed against PBS and degassed before use. The envelope protein concentration in the sample cell is approximately 4 μM, and the sCD4 concentration in the syringe is 40 μM; the reference cell contains degassed Milli-Q water. Envelope proteins in the sample cell are titrated to saturation by the stepwise addition of 10 μl of sCD4 from the syringe at 400-s intervals at 37° C. The heat evolved upon each injection of sCD4 is calculated from the integral of the calorimetric signal. The heat of dilution of sCD4 is subtracted from the heat of reaction with gp120 in order to obtain the heat released due to the Env-sCD4 binding reaction. Molar concentrations of the proteins are calculated by standard methods, and the values for enthalpy (ΔH), entropy (ΔS), and the association constant ($K_a$) are calculated by fitting the data to a nonlinear least-squares analysis using Origin software.

Antigenic Analysis

The antigenicities of uncrosslinked/non-stabilized and dityrosine crosslinked/stabilized envelope proteins are determined by standard enzyme-linked immunosorbent assay (ELISA) using a panel of non-neutralizing, neutralizing, and broadly neutralizing antibodies, including the F105, b12, 2F5, 4E10, D5, 17b (+/−soluble CD4), 15e, D5, b6, PA1, CA13, G3-519, 2G12, and 7B2 antibodies.

Corning high-protein-binding ELISA plates are coated with 400 ng per well of *Galanthus nivalis* lectin (catalog no. L8275-5MG; Sigma) in 100 μl of PBS (pH 7.4) at 4° C. overnight. The next day, the lectin is removed, the wells are blocked for 3 hrs at room temperature with PBS containing 2% fat-free milk and 4% fetal calf serum, and the wells are washes five times with wash buffer (PBS with 0.2% Tween 20). Subsequently, the wells are incubated with 200 ng of crosslinked and uncrosslinked Env protein in 100 μl of PBS for 2 hrs at room temperature, followed by five washes and incubation with 100 μl of different monoclonal antibody solutions that are fivefold serially diluted starting with 20 μg/ml of the initial concentration in dilution buffer (1:10-diluted blocking buffer), and incubated for 1 hr at room temperature. The wells then are washed and incubated for 1 hr at room temperature with 100 μl of a horseradish peroxidase (HRP)-conjugated anti-human IgG (catalog no. 109-036-097; Jackson ImmunoResearch Laboratories, Inc.) solution at a 1:10,000 dilution in antibody dilution buffer. After five subsequent washes, 100 μl of the colorimetric peroxide enzyme immunoassay substrate (3,3',5,5'-tetramethylbenzidine; Bio-Rad) is added to each well, and the reaction is stopped by adding 100 μl of 1M sulfuric acid to the mixture. The OD of the wells is read at 450 nm using an ELISA plate reader. All samples are run in duplicate. The average OD of negative control wells containing bovine serum albumin (BSA) is subtracted from the average OD of experimental wells to obtain final OD values.

Immunization and Characterization of Immune Sera
Immunization

New Zealand White rabbits (approximately 12 week old females) are inoculated by intradermal injection with 125 μg of proteins emulsified in a 1:1 dilution of Ribi adjuvant (Corixa, Hamilton, Mont.) in a total volume of 1 ml. One inoculation of 500 μl each is administered in each hind leg within 2 hrs of preparation. Boosting inoculations are injected at 4-week intervals. Test bleeds are collected 10 days after each booster inoculation. Blood is incubated at room temperature for 2 hrs for clotting and centrifugated for 10 min at 2,000×g, and the clotted components are discarded. The serum is heat inactivated at 56° C. for 1 hr and stored at −20° C. for subsequent analysis.

Characterization of Immunized Sera

To determine the anti-gp140 antibody titers in immunized sera, ELISA assays are preformed, essentially as described above. Plates are coated with 200 ng of wild-type gp120 and gp41 monomeric, dimeric and trimeric spike complex Env protein in 100 µl of PBS per well. After blocking and washes, fivefold serial dilutions (starting at 1/200) of the sera from immunized rabbits are added in duplicate wells and incubated for 2 hrs at room temperature. Following washes, the wells are incubated with a 1:10,000 dilution of HRP-conjugated anti-rabbit IgG (catalog no. 111-035-046; Jackson ImmunoResearch Laboratories, Inc.) and developed with HRP substrate, and the ODs are read at 450 nm.

Neutralization and Virus Entry Assays

Pseudotyped Virus Preparation

HIV-1 is pseudotyped with selected envelope glycoproteins by cotransfection of an env expression vector and viral genomic DNA with a deletion of Env into 293T cells. Following the production of pseudotyped virus, a luciferase-based neutralization assay is performed as previously described in detail in Li et al. 2006 (Li et al., 2006. Characterization of antibody responses elicited by human immunodeficiency virus type 1 primary isolate trimeric and monomeric envelope glycoproteins in selected adjuvants. J Virol 80: 1414-1426) and Li et al., 2005 (Li et al., 2005 Human immunodeficiency virus type 1 env clones from acute and early subtype B infections for standardized assessments of vaccine-elicited neutralizing antibodies. J Virol 79: 10108-10125).

HIV Infection Assay

TZM-bl cells expressing CD4, CXCR4, and CCR5, and containing Tat-responsive reporter genes for firefly luciferase and the *Escherichia coli* β-galactosidase gene under the regulatory control of the HIV-1 long terminal repeat, are used for HIV-1 infection. The level of HIV-1 infection is quantified by measuring relative light units (RLU) of luminescence, which is directly proportional to the amount of viral infection. The assays are performed using a 96-well microtiter plate format with 10,000 TZM-bl cells per well. This HIV infection assay is described in detail in Li et al., 2005 (Li et al., 2005 Human immunodeficiency virus type 1 env clones from acute and early subtype B infections for standardized assessments of vaccine-elicited neutralizing antibodies. J Virol 79: 10108-10125).

Neutralization Assays

For neutralization assays, each pseudotyped virus stock is diluted to a level that produced approximately 100,000 to 500,000 RLU. The percentage of virus neutralization by each immune serum sample is derived by calculating the reduction in RLUs in the test wells compared to the RLUs in the wells containing pre-immune serum from the corresponding animal. To control for nonspecific neutralization in protein-immunized rabbits, sera from two animals immunized with BSA are analyzed. All serum samples are also assayed for neutralizing activity against a pseudovirus expressing the amphotropic murine leukemia virus envelope to test for non-HIV-1-specific plasma effects. Neutralization of HIV-2 strain 7312A/V434M is performed as described in Decker et al., 2005 (Decker et al., 2005. Antigenic Conservation and immunogenicity of the HIV coreceptor binding site. J Exp Med 201: 1407-1419). Pseudovirus stock is treated with mock media or with 0.5 µg/ml of sCD4 (50% inhibitory concentration [IC50] for entry of this virus) for 1 hr before adding sera. The remainder of the assay is done as described above. To calculate the percent neutralization with sCD4 present in the assay, the baseline RLU is the value measured with virus plus sCD4 and no serum. To obtain IC50 data, fivefold serial dilutions of immune sera are incubated with viruses before infection of target cells. Antiserum dose-response curves are fit with a nonlinear function, and the IC50 for the corresponding virus is calculated by a least-squares regression analysis. Statistical analysis of the IC50 titers is performed with the unpaired t test (GraphPad Prism software package 3.0; GraphPad Software Inc., San Diego, Calif.).

Virus Entry Assays

WT and mutant pseudotyped YU2 viruses are produced by cotransfection of envelope glycoprotein expressor plasmids and viral genomic DNA with a deletion of the env gene into 293T cells, as described above. Pseudovirus titers are adjusted by p24 ELISA (Beckman Coulter) according to the manufacturer's protocol. Equivalent doses of virus suspended in a 40 µl volume are then mixed with 20 µl of TZM-bl cells (10,000 cells) and 10 µl of medium on 96-well plates and incubated overnight at 37° C. The following day, 130 µl of cell culture medium is added to each well and incubated for an additional 24 hrs. Cell culture medium then is removed from all wells, and 50 µl of cell lysis buffer (Promega, Madison, Wis.) is added. Thirty microliters of cell lysis supernatant is transferred onto a new plate containing substrate for the measurement of luminescence using a luminometer. The RLU produced by the wells are measured and used to calculate viral entry. To determine antibody-mediated neutralization of HIV-1 entry, each viral inoculum is preincubated with fourfold serial dilutions of antibody in 50 µl of medium for 1 h at 37° C. After virus-antibody incubation, the TZM-bl target cells are added to the wells Example 2

The most potent broadly neutralizing antibodies to HIV bind Env trimer-specific quaternary neutralizing epitopes (QNEs), but the Env trimer is too unstable to maintain its quaternary structure and present theses QNEs. In preliminary studies using a recombinant, soluble HIV Env trimer, we have demonstrated that we can use dityrosine (DT) crosslinking to conformationally lock the Env immunogen in its native, trimeric conformation, so that it improves binding to the most potent HIV quaternary broadly neutralizing antibodies. Antibody responses to these epitopes have the potential to be protective against the enormous breadth of HIV strains and clades in circulation. By applying targeted DT "staples" to covalently cross-link the trimerizing interactions at the apex of the native spike, we have successfully engineered conformationally locked, soluble Env trimers with fully preserved QNEs.

Figure 1B:
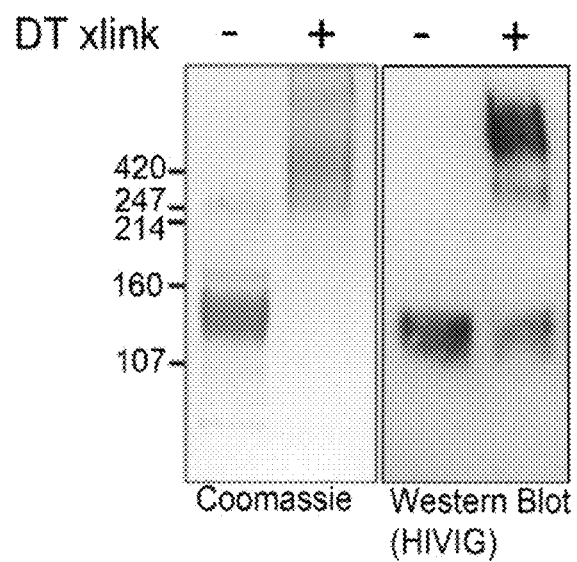

The HIV envelope spike is trimerized through well characterized, interactions at its base as well as interactions at the spike's apex. In order to stabilize the trimerizing interactions at the apex of the spike, we introduced tyrosine substitutions to generate engineered HIV spike proteins, and then expressed, purified, and DT cross-linked the engineered proteins. FIG. 1A-B shows the results of an analysis of DT cross-linked Env gp140 trimers. DTspecific spectrofluorometry identified and quantified DT crosslinks in the HIV Env gp140 variant with tyrosine substitution in V1/V2 before and after DT cross-linking. Coomassie staining and a-HIV Env Western blot of purified gp140 trimer are also shown in FIG. 1A-B. These confirmed the presence of intermolecular cross-linking.

Figure 2:
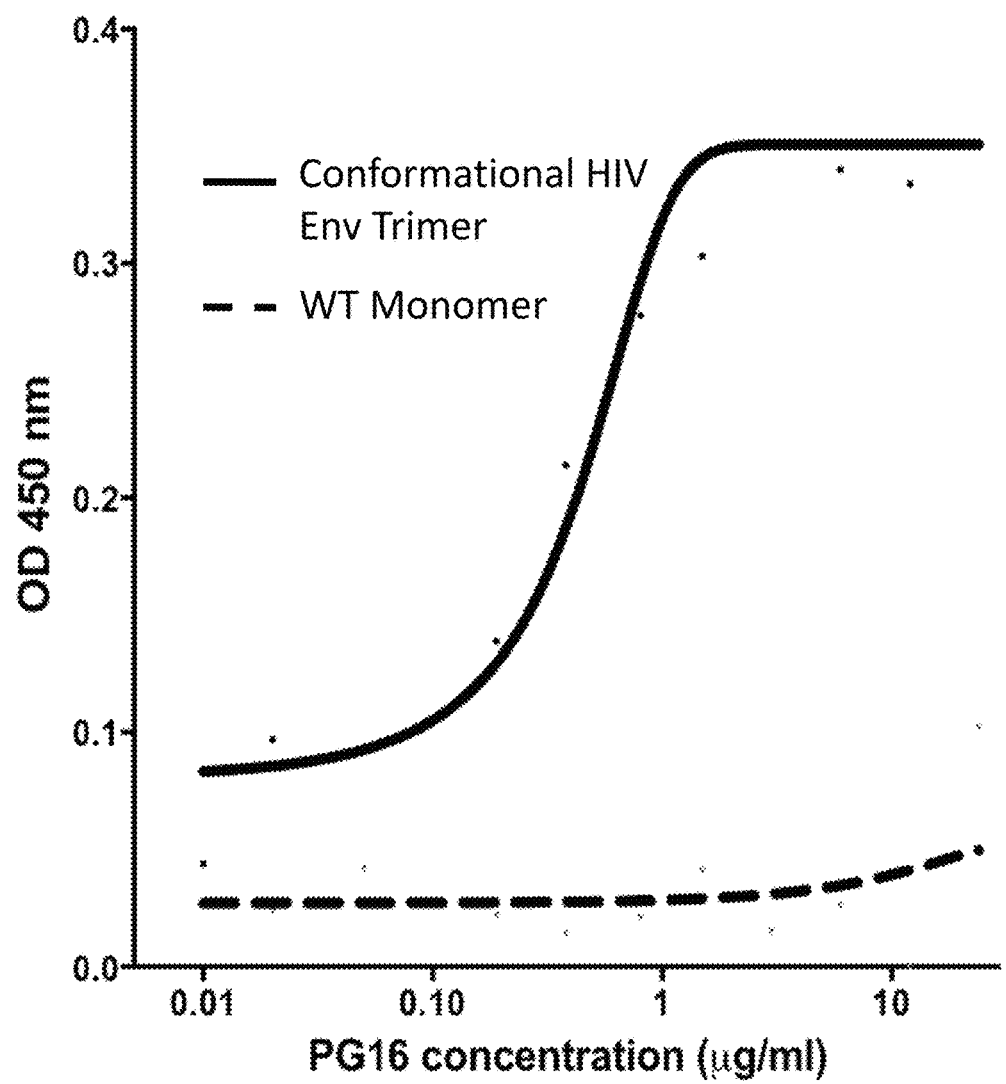
FIG. 2. Binding of wild type HIV Env protomer and conformationally locked HIV Env trimer to varying concentrations of the broadly neutralizing antibody PG16 was measured by enzyme-linked immunosorbent assay (ELISA). The lower line on the graph represents binding of wild type (WT) HIV Env protomer to varying concentrations of PG16, while the upper line represents binding of a conformationally locked HIV Env trimer to varying concentrations of PG16.

By fluorescence, we identified seven variants that formed intermolecular, trimerizing cross-links with an average of 80%+ efficiency prior to any optimization, as quantified using DT-specific excitation (320 nm) and emission (405 nm) wavelengths. We assayed the ability of these constructs to bind conformational and trimer-specific broadly neutralizing antibodies. DT crosslinking fully preserved binding of the anti-CD4 binding site on the broadly neutralizing antibody b12 (which binds both protomers and trimers) and the anti-V2 broadly neutralizing antibody PG9 (which preferentially binds trimers, but also binds monomers). In addition, conformational locking also significantly reduced binding to non-neutralizing monoclonal antibodies (such as b6 and b13) in ELISA assays (data not shown). The position of the DT bonds was confirmed by tandem mass spectrometry (MS/MS) of tryptic fragments of the DT-Env trimer. Importantly, we found that a conformationally locked HIV Env trimer binds significantly better to one of the most extremely broadly neutralizing and potent anti-HIV Env broadly neutralizing antibodies, PG16, by comparison to the wild type protomer. FIG. 2 provides the results of an ELISA assay. The lower line represents binding of a wild type (WT) HIV Env protomer to PG16, while the upper line represents binding of a conformationally locked trimer to PG16. The PG16 epitope is only presented on the native/functional HIV envelope trimer. Improved PG16 binding correlated with a significant reduction in binding to a poorly neutralizing anti-V2 monoclonal antibody, CH58 (data not shown), that binds an α-helical conformer of an overlapping epitope that PG16 binds as a β-sheet. The "DT-locked" soluble HIV Env trimer can be tested in various assays to assess its immunogenicity in animals and other characteristics. Suitable assays include those described in the previous Examples, those described elsewhere in the specification, those known in the art.

The invention as described herein is not to be limited in scope to the specific embodiments and Examples provided, which are intended to provide illustrations of several aspects of the invention. Various modifications of the specific embodiments and examples described here will be apparent to those skilled in the art from the foregoing description. Such modifications are also intended to fall within the scope of the present invention.

A number of references are cited herein. For the purposes of jurisdictions which allow incorporation by reference only, the entire disclosures of each of the references cited herein are incorporated by reference in their entireties.

The present invention may also be further described and defined in terms of the following claims.

The invention claimed is:

1. A method for producing an HIV immunogen comprising: obtaining a stabilized HIV trimeric spike protein complex which has the capacity to elicit a neutralizing or a broadly neutralizing humoral response, wherein the stabilized HIV trimeric spike protein complex is produced by introducing at least two dityrosine cross-links between amino acids at positions 143 and 150 and amino acids at positions 160 and 180 in the V1/V2 loop distal to the stem.

2. The method of claim 1, further comprising introducing into the HIV trimeric spike protein complex one or more point mutations to tyrosine between amino acid positions 143 and 150 and/or amino acid positions 160 and 180 in the V1/V2 loop distal to the stem, prior to introducing the dityrosine cross-links.

3. The method of claim 1, further comprising performing an assay to assess the ability of the stabilized HIV trimeric spike protein complex to bind to a neutralizing antibody, bind to a broadly neutralizing antibody, bind to and activate B cell receptors, elicit an antibody response in an animal, elicit a protective antibody response in an animal, elicit production of neutralizing antibodies in an animal, elicit production of broadly neutralizing antibodies in an animal, elicit a protective immune response in an animal, and/or elicit production of antibodies that recognize quaternary neutralizing epitopes in an animal.

4. The method of claim 1, wherein at least one of the tyrosines in at least one of the dityrosine cross-links originates from a point mutation to tyrosine.

5. An HIV trimeric spike protein complex comprising at least two dityrosine cross-links, wherein the dityrosine cross-links are between positions 143 and 150, and between positions 160 and 180 in the V1/V2 loop distal to the stem.

6. The protein complex of claim 5, wherein at least one of the tyrosines in at least one of the dityrosine cross-links originates from a point mutation to tyrosine.

7. A pharmaceutical composition comprising: a pharmaceutically effective amount of an HIV trimeric spike protein complex made using the method of claim 1 and a pharmaceutically acceptable carrier.

8. A pharmaceutical composition comprising: a pharmaceutically effective amount of an HIV trimeric spike protein complex according to claim 5 and a pharmaceutically acceptable carrier.

* * * * *